(12) United States Patent
Bergo

(10) Patent No.: US 11,391,729 B2
(45) Date of Patent: Jul. 19, 2022

(54) MULTIPLEXED BEAD ARRAYS FOR PROTEOMICS

(71) Applicant: Adeptrix Corp., Beverly, MA (US)

(72) Inventor: Vladislav B. Bergo, Boston, MA (US)

(73) Assignee: ADEPTRIX CORP., Beverly, MA (US)

(*) Notice: Subject to any disclaimer, the term of this patent is extended or adjusted under 35 U.S.C. 154(b) by 129 days.

(21) Appl. No.: 16/125,164

(22) Filed: Sep. 7, 2018

(65) Prior Publication Data

US 2019/0072546 A1 Mar. 7, 2019

Related U.S. Application Data

(60) Provisional application No. 62/555,235, filed on Sep. 7, 2017.

(51) Int. Cl.
*G01N 33/543* (2006.01)
*G01N 33/68* (2006.01)
*G01N 27/74* (2006.01)

(52) U.S. Cl.
CPC .. *G01N 33/54306* (2013.01); *G01N 33/54313* (2013.01); *G01N 33/6845* (2013.01); *G01N 33/6848* (2013.01); *G01N 33/6854* (2013.01); *G01N 27/745* (2013.01); *G01N 2440/00* (2013.01)

(58) Field of Classification Search
CPC ........... G01N 33/6848; G01N 33/6845; G01N 27/745
See application file for complete search history.

(56) References Cited

U.S. PATENT DOCUMENTS

| | | | |
|---|---|---|---|
| 4,732,811 | A | 3/1988 | Margel |
| 6,284,197 | B1 | 9/2001 | Abbott et al. |
| 7,033,754 | B2 | 4/2006 | Chee et al. |
| 7,439,056 | B2 | 10/2008 | Duffy et al. |
| 7,622,294 | B2 | 11/2009 | Walt et al. |
| 7,846,748 | B2 | 12/2010 | Borchers |
| 7,858,560 | B2 | 12/2010 | Koester et al. |
| 9,395,360 | B2 | 7/2016 | Trau et al. |
| 9,513,285 | B2 | 12/2016 | Lim et al. |
| 9,523,680 | B2 | 12/2016 | Lim et al. |
| 9,618,520 | B2 | 4/2017 | Bergo |
| 10,101,336 | B2 | 10/2018 | Bergo |
| 10,451,631 | B2 | 10/2019 | Bergo |
| 2003/0073228 | A1 | 4/2003 | Duffy et al. |
| 2003/0124029 | A1 | 7/2003 | Webb et al. |
| 2005/0266407 | A1 | 12/2005 | Chee et al. |
| 2006/0003366 | A1 | 1/2006 | DiCesare |
| 2006/0014212 | A1 | 1/2006 | Benkovic et al. |
| 2006/0110733 | A1 | 5/2006 | Toohey et al. |
| 2006/0234251 | A1 | 10/2006 | Akhavan-Tafti |
| 2008/0176340 | A1 | 7/2008 | Soldo et al. |
| 2008/0254481 | A1 | 10/2008 | Love et al. |
| 2009/0071827 | A1* | 3/2009 | Cargile .............. G01N 33/6848 204/644 |
| 2009/0270278 | A1 | 10/2009 | Lim et al. |
| 2010/0009344 | A1 | 1/2010 | Israel et al. |
| 2010/0084328 | A1* | 4/2010 | Ma ..................... B01J 20/285 210/198.2 |
| 2010/0256015 | A1 | 10/2010 | Lim et al. |
| 2010/0304978 | A1 | 12/2010 | Deng et al. |
| 2010/0317542 | A1 | 12/2010 | Lim et al. |
| 2011/0212848 | A1 | 9/2011 | Duffy et al. |
| 2011/0245097 | A1 | 10/2011 | Rissin et al. |
| 2011/0312897 | A1 | 12/2011 | Allis et al. |
| 2012/0065088 | A1 | 3/2012 | Danielsen et al. |
| 2012/0077688 | A1* | 3/2012 | Bergo ................ G01N 33/6848 506/9 |
| 2012/0202709 | A1 | 8/2012 | Bergo |
| 2012/0244593 | A1 | 9/2012 | Huang et al. |
| 2013/0244230 | A1* | 9/2013 | Luider ..................... C12Q 1/02 435/6.1 |
| 2014/0323330 | A1 | 10/2014 | Bergo |
| 2015/0253341 | A1 | 9/2015 | McAvoy et al. |
| 2016/0008785 | A1 | 1/2016 | Bergo |
| 2017/0176453 | A1 | 6/2017 | Bergo |
| 2019/0004038 | A1 | 1/2019 | Lim et al. |
| 2020/0011877 | A1 | 1/2020 | Bergo |
| 2021/0018513 | A1 | 1/2021 | Bergo |

FOREIGN PATENT DOCUMENTS

| | | |
|---|---|---|
| WO | 2007000669 A2 | 1/2007 |
| WO | 2007014267 A2 | 2/2007 |
| WO | 2012109460 A1 | 8/2012 |
| WO | 2014176435 A1 | 11/2015 |
| WO | 2019051254 A1 | 3/2019 |

OTHER PUBLICATIONS

International Search Report dated Feb. 1, 2019, in PCT Application No. PCT/US18/49995, the PCT counterpart to the present application.
Written Opinion dated Feb. 1, 2019, in PCT Application No. PCT/US18/49995, the PCT counterpart to the present application.
Cammarata et al., "An Affinity Capture MALDI TOF MS Method for High Density Multiplexed Profiling of Total and PTM Protein Biomarker Panels," Proceedings of American Society for Mass Spectrometry 64th Annual Meeting, San Antonio, TX (Jun. 5-9, 2016); retrieved from the Internet on Dec. 21, 2018 at https://www.adeptrix.com/pdf/2016_ASMS_Adeptrix-Poster_051716_FINAL.pdf.
Cell Signaling Technology #4370. Phospho-p44/42 MAPK (Erk 1/2) (Thr202/Tyr204) (D13.14.4E) XP Rabbit mAb (2014); retrieved from the Internet on Dec. 21, 2018 at https://media.cellsignal.com/pdf/4370.pdf.

(Continued)

*Primary Examiner* — Changhwa J Cheu

(74) *Attorney, Agent, or Firm* — Kriegsman & Kriegsman

(57) ABSTRACT

Bead arrays suitable for analysis by mass spectrometry are disclosed. In an embodiment, a bead array includes multiple reactive sites, each of the reactive sites being capable of binding multiple distinct target analytes.

11 Claims, 5 Drawing Sheets

Specification includes a Sequence Listing.

(56) References Cited

OTHER PUBLICATIONS

Abstract of Nagy et al., "Selective Monoclonal Antibody Recognition and Cellular Localization of an Unphosphorylated Form of Connexin43," Experimental Cell Research, 236(1):127-136 (1997).
Uniprot accession P06493. CDK1_Human (May 10, 2017); retrieved from the Internet on Dec. 21, 2018 at https://www.uniprot.org/uniprot/P06493.txt?version=221.
Anderson et al., "Precision of Heavy-Light Peptide Ratios Measured by MALDI-TOF Mass Spectrometry," Journal of Proteome Research, 11:1868-1878 (2012).
Razavi et al., "MALDI Immunoscreening (MiSCREEN): A Method for Selection of Anti-peptide Monoclonal Antibodies For Use in Immunoproteomics," J Immunol Methods, 364(1-2):50-64 (2011).
Popp et al., "Immuno-MALDI (iMALDI) for quantifying AKT1 and AKT2 in breast and colorectal cancer cell lines and tumors," Analytical Chemistry, 89(19):10592-10600 (2017).
Goodman et al., "Affi-BAMS: A High Throughput Immunoaffinity Enrichment Assay with Detection by LAESI MS and MALDI MS," Poster Presentation at 65th Annual ASMS Conference, Jun. 6, 2017, Indianapolis, Indiana.
Mamaev et al., "Affi-BAMS™: a MALDI MS Based Immuno-Affinity Platform for Monitoring Total Protein and PTM Changes with a Multiplex Capacity of over 1,000 Analytes," Poster Presentation at MSACL 2017 US Annual Conference, Jan. 24, 2017, Palm Springs, California.
Mamaev et al., "Bead Assisted Mass Spectrometry (BAMS): An Affinity Capture MALDI TOF MS Method for Multiplexed Biomarker Screening," Poster Presentation at 66th Annual ASMS Conference, Jun. 5, 2018, San Diego, California.
Mamaev et al., "Bead Assisted Mass Spectrometry (BAMS): A Robust Affinity Capture, MS Method for Multiplexed Biomarker Profiling," Poster Presentation at 66th Annual ASMS Conference, Jun. 5, 2018, San Diego, California.
Astle et al., "Seamless Bead to Microarray Screening: Rapid Identification of the Highest Affinity Protein Ligands from Large Combinatorial Libraries," Chemistry and Biology, 17:38-45 (2010).
Lam et al., "The 'One-Bead-One-Compound' Combinatorial Library Method," Chem Rev, 97:411-448 (1997).
Tannu et al., "Two-dimensional fluorescence difference gel electrophoresis for comparative proteomics profiling," Nat Protoc., 1(4):1732-1742 (2006).
Horiuchi et al., "Microarrays for the Functional Analysis of the Chemical-Kinase Interactome," Society for Biomolecular Sciences, Journal of Biomolecular Screening, 11(1):48-56 (2008).
Salmon et al., "Discovery of biologically active peptides in random libraries: Solution-phase testing after staged orthogonal release from resin beads," Proc. Natl. Acad. Sci. USA, 90:11708-11712 (1993).
Salmon et al., "High-volume cellular screening for anticancer agents with combinatorial chemical libraries: A new methodology," Molecular Diversity, 2:57-63 (1996).
Yang et al., "Primer on Agar-Based Microbial Imaging Mass Spectrometry," Journal of Bacteriology, 194:6023-6028 (2012).
Lehar et al., "Synergistic drug combinations tend to improve therapeutically relevant selectivity," Nature Biotechnology, 27:663-666 (2009).
Adamo et al., "Gefitinib in lung cancer therapy," Cancer Biology & Therapy, 8:206-212 (2009).
Trummer et al., "Pharmaceutics, Preformulation and Drug Delivery Physicochemical Properties of Epidermal Grwoth Factor Receptor Inhibitors and Development of a Nanoliposomal Formulation of Gefitinib," Journal of Pharmaceutical Sciences, 101:2763-2776 (2012).
Townsend et al., "Jeffamine Derivatized TentaGel Beads and Poly(dimethylsiloxane Microbead Cassettes for Ultrahigh-Throughput in Situ Releasable Solution-Phase Cell-Based Screening of One-Bead-One-Compound Combinatorial Small Molecule Libraries," J. Comb. Chem., 12:700-712 (2010).
Bake et al., "Multiplexed Spectroscopic Detections," Annual Rev. Anal. Chem., 1:515-547 (2008).
Chughtai et al., "Mass Spectrometric Imaging for biomedical tissue analysis," NIH Public Access, Chem. Rev., Author Manuscript, 1-87 (2010).
Drancourt, "Detection of Microorganisms in Blood Specimens Using Matrix-Assisted Laser Desorption Ionization Time-of-Flight Mass Spectrometry: A Review," Clinical Microbiology and Infection, 16:1620-1625 (2010).
Duncan et al., "Quantitative Matrix-Assisted Laser Desorption/Ionization Mass Spectrometry," Briefings in Functional Genomics and Proteomics, 7(5):355-370 (2008).
Ayoglu et al., "Affinity proteomics within rare diseases: a BIO-NMD study for blood biomarkers of muscular dystrophies," EMBO Molecular Medicine, 6(7):918-36 (2014).
Barbee et al., "Multiplexed protein detection using antibody-conjugated microbead arrays in a microfabricated electrophoretic device," Lab Chip, 10:3084-3093 (2010).
Chen et al., "Current applications of antibody microarrays," Clinical Proteomics, 15:1-15 (2018).
Qi et al., "The convergent chemical synthesis of histone H3 protein for site-specific acetylation at Lys56 and ubiquitination at Lys122," Chem. Commun., 53:4148-4151 (2017).
Ito et al., "Proteolytic Cleavage of High Mobility Group Box 1 Protein by Thrombin-Thrombomodulin Complexes," Arterioscler Thromb Vasc Biol., 29:1825-1830 (2008).
Pending U.S. Appl. No. 17/127,402, inventor Vladislav B. Bergo, filed Dec. 18, 2020.
Pending U.S. Appl. No. 17/187,388, inventor Vladislav B. Bergo, filed Feb. 26, 2021.
Cammarata et al., "Affinity Capture MALDI TOF MS Method for High Density Multiplexed Profiling of Total and PTM Protein Biomarker Panels," Proceedings of American Society for Mass Spectrometry 64th Annual Meeting, San Antonio, TX (Jun. 5-9, 2016), together with enlarged copy of data from Fig. 8.

\* cited by examiner

MULTIPLEXED BEAD ARRAYS FOR PROTEOMICS

CROSS-REFERENCE TO RELATED APPLICATIONS

The present application claims the benefit under 35 U.S.C. 119(e) of U.S. Provisional Patent Application No. 62/555,235, inventor Vladislav B. Bergo, filed Sep. 7, 2017, the disclosure of which is incorporated herein by reference.

FEDERALLY SPONSORED RESEARCH OR DEVELOPMENT

This invention was made with government support under grant number GM103348 awarded by the National Institutes of Health (NIH) and grant number 1456224 awarded by the National Science Foundation (NSF). The government has certain rights in the invention.

SEQUENCE LISTING

The instant application contains a Sequence Listing which has been submitted electronically in ASCII format and is hereby incorporated by reference in its entirety. Said ASCII copy, created on Sep. 7, 2018, is named 84025A_SL.txt and is 14,636 bytes in size.

FIELD

The embodiments disclosed herein relate generally to the field of bead arrays and more specifically to the field of encoding beads in bead arrays. The embodiments disclosed herein also relate to the fields of bead-based analytical assays, proteomics, protein quantification, affinity separations and mass spectrometry.

BACKGROUND

A biological array is a multiplexed analytical platform technology that has found multiple applications in Life Sciences, particularly in the fields of genomics, metabolomics, lipidomics, glycomics, proteomics, histology and cytology. A biological array usually features a large number of distinct capture agents immobilized on a solid support, such as a glass microscope slide or beads. A capture agent is capable of binding a target analyte. Depending upon the chosen type of solid support, biological arrays can be classified either as printed arrays or bead arrays. A major difference between printed arrays and bead arrays is that bead arrays often lack positional encoding. Consequently, the identity of a capture agent, which is bound to a specific bead, may not be inferred from the spatial location of the bead and other means of bead encoding must be utilized.

Various methods of encoding bead arrays are known in the art. Such methods utilize optical labels, fluorescent labels, optical barcodes, identifier binding ligands and mass tags.

Certain types of bead arrays do not require bead encoding. For example, it may be possible to directly analyze a capture agent by mass spectrometry and identify such capture agent based on its measured molecular weight, digestion profile or MS-MS fragmentation profile.

It may be also possible to directly analyze a target analyte by mass spectrometry and identify such target analyte based on its measured molecular weight, digestion profile or MS-MS fragmentation profile.

U.S. Pat. No. 7,846,748 entitled "Methods of quantitation and identification of peptides and proteins" discloses using Matrix-Assisted Laser Desorption Ionization Mass Spectrometry (MALDI MS) to analyze a mixture of unlabeled and isotopically labeled peptides bound to a single bead. It is disclosed that the amino acid sequence of a bead-bound peptide may be determined by measuring the peptide fragmentation profile using tandem MALDI mass spectrometry (MALDI MS-MS) followed by database searching or by performing de novo identification. The possibility of quantitative measurement of peptide abundance is also disclosed, which requires the use of isotope labeled peptides, namely peptides containing $^2$H and $^{18}$O isotopes.

U.S. Pat. No. 7,033,754 entitled "Decoding of array sensors with microspheres" discloses the use of mass spectrometry to identify an identifier binding ligand (IBL) bound to a microsphere, which already contains a bioactive agent. In the disclosed approach the IBL functions similarly to a bead mass tag. It is also disclosed that the characterization of the bioactive agent may be performed directly by using mass spectroscopy.

U.S. Pat. No. 9,618,520 entitled "Microarray compositions and methods of their use", the entirety of which is incorporated herein by reference, discloses that microarrays may possess no conventional means of encoding the active agent. Consequently, an active agent may serve as its own code and the microarray decoding procedure may comprise releasing the active agent from its corresponding bead followed by identification of the active agent using mass spectrometry.

U.S. patent application Ser. No. 13/369,939, Publication No. US 2012-0202709 A1, the entirety of which is incorporated herein by reference, discloses providing information about molecular weights of compounds that are present or may be present within a bead array. Such compounds may include capture agents, targets, probes, secondary probes, linkers and bead mass tags. It is disclosed that the molecular weight information may be used to guide acquisition of mass spectrometric data and also to identify analytes present on individual beads.

An article entitled "MALDI Immunoscreening (MiSCREEN): A Method for Selection of Anti-peptide Monoclonal Antibodies For Use in Immunoproteomics" (Razawi M et al, J. Immunol. Methods 2011, 364, 50-64) discloses anti-peptide antibodies suitable for immunoaffinity enrichment. It also discloses a table containing a list of protein targets, corresponding tryptic peptides, their amino acid sequences and predicted molecular weights.

An article entitled "Precision of Heavy-Light Peptide Ratios Measured by MALDI-TOF Mass Spectrometry" (Anderson N L et al, J. Proteome Res. 2012, 11, 1868-1878) discloses a MALDI TOF mass spectrum recorded after incubation of digested human plasma with an anti-peptide antibody conjugated to protein G Dynabeads. Multiple (over 20) distinct peaks were detected in the 1,000-1,500 m/z region of the mass spectrum. Several of these peaks were assigned to peptides that were specifically captured by the bead-conjugated antibody. Another peak was assigned to a proteolytic peptide derived from human serum albumin, which was non-specifically bound to the antibody-conjugated bead. The majority of peaks were not assigned to a particular analyte and their origins remained unknown.

The prior art does not teach or suggest target-encoded bead arrays, in which a reactive site is encoded solely by molecular weights of target analytes that specifically bind to a capture agent of the reactive site. In particular, the prior art does not disclose target-encoded bead arrays in which a capture agent of a reactive site is capable of binding two, three, four or a greater number of distinct target analytes and the reactive site is encoded by a combination of two, three, four or a greater number of values, each of the values being derived from a molecular weight of a target analyte that specifically binds to the capture agent of the reactive site.

Therefore, there is still a need for methods and compositions that would enable analysis of bead arrays.

SUMMARY

In one aspect, the present specification describes a bead array that includes at least a first reactive site and a second reactive site. The first reactive site includes a first bead and a first capture agent that is associated with the first bead. The first capture agent specifically recognizes a naturally occurring epitope and specifically binds at least two distinct targets that contain such epitope. The distinct targets may be proteinaceous compounds that have distinct molecular weights. The distinct targets may be proteolytic fragments of a single precursor protein or proteolytic fragments of distinct precursor proteins. The second reactive site includes a second bead and a second capture agent that is chemically distinct from the first capture agent, is associated with the second bead and specifically recognizes an epitope that is not recognized by the capture agent of the first reactive site. Each of the first and the second reactive sites is associated with a unique combination that includes at least two distinct values, which are derived from the molecular weights of targets that specifically bind to the corresponding reactive site. The combination associated with the first reactive site is distinct from the combination associated with the second reactive site.

In another aspect, the present specification describes a method of performing affinity binding using a bead array, which includes the steps of contacting a bead array with a sample, binding a first target and a second target from the sample to a first reactive site of the bead array and binding a third target from the sample to a second reactive site of the bead array. The first and the second reactive sites contain a bead and a capture agent, the capture agent of the first reactive site being different from the capture agent of the second reactive site. The first target and the second target are proteinaceous compounds that have molecular weights less than 5000 Da and contain a naturally occurring epitope, which is recognized by a capture agent of the first reactive site. The third target contains an epitope, which is recognized by a capture agent of the second reactive site and not recognized by the capture agent of the first reactive site.

In yet another aspect, the present specification describes a method of decoding a bead array, which includes the steps of receiving a mass spectrum that was produced by analyzing a reactive site of the microarray, detecting a first signal and a second signal in the mass spectrum and verifying that m/z values of the first signal and of the second signal or equivalents thereof match values, which are present in a combination associated with at least one of the reactive sites of the microarray.

In yet another aspect, the present specification describes a method of making a bead array. The method includes the step of evaluating individual reactive sites of a bead array to determine the identity and molecular weights of target analytes, which may bind to each reactive site, either specifically or non-specifically. The method may optionally include the step of entering information about the identity and molecular weights of the target analytes into a decoding table, which is then included with the bead array.

In yet another aspect, the present specification describes several methods of identifying a target analyte within a bead array. Some of the described methods involve measuring a value derived from a molecular weight of the target analyte and subsequently using a decoding table provided with the microarray to determine the identity of the target analyte. The described methods may be utilized to analyze various types of biological samples, including cell free protein transcription-translation reactions, bacterial cell cultures, mammalian cell cultures, cell culture supernatants, animal models, xenografts, tissue biopsies, biofluids and others.

The analytical methods and compositions described in this specification may be utilized in a broad range of applications including basic research, pharmaceutical drug discovery and drug development, disease diagnostics and prognostics, biomarker discovery and validation, personalized medicine, precision medicine, systems biology and others.

DESCRIPTION OF FIGURES

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

DETAILED DESCRIPTION

The terms "microarray" and "bead array" are used interchangeably throughout the instant specification and refer to a group that includes at least two reactive sites.

The term "reactive site" refers to a combination of a bead and a capture agent that is associated with the bead.

The term "capture agent" refers to a molecule or a molecular complex that is capable of specifically binding a compound. A non-limiting example of a capture agent is a monoclonal antibody. A singular form of the term "capture agent" may refer to a plurality of molecules or a plurality of molecular complexes. For example it may refer to a plurality of antibody molecules.

The terms "target analyte" and "target" are used interchangeably throughout the instant specification and generally refer to a binding partner of a capture agent. A non-limiting example of a target analyte is a peptide. Singular forms of the terms "target analyte" and "target" may refer to a plurality of molecules, e.g. a plurality of peptide molecules.

The terms "peptide" and "polypeptide" are used interchangeably throughout the instant specification and refer to a compound that contains at least two amino acids linked by an amide bond, which is also known as a peptide bond.

The term "protein" has the same meaning as commonly used in the fields of biochemistry, biophysics and molecular biology. It generally refers to a molecule or a molecular complex that contains at least one polypeptide.

The term "proteinaceous compound" encompasses a peptide, a polypeptide and a protein.

The terms "well" and "microwell" are used interchangeably throughout the instant specification and refer to a topological feature such as a pit or a depression that is able to hold a liquid medium, a particle or both.

The term "value" is commonly defined as a numerical amount denoted by an algebraic term; a magnitude, quantity, or number.

Figures 1A, 1B:
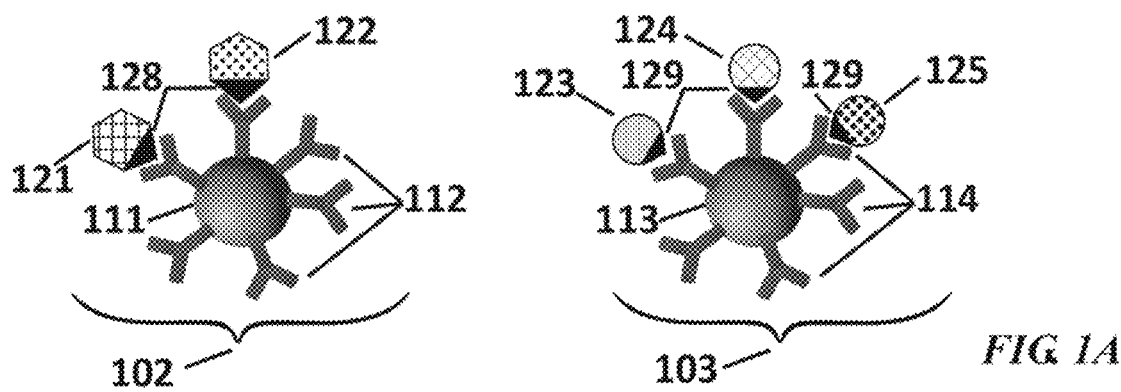
FIG. 1A schematically depicts a bead array that includes several distinct reactive sites. Each of the reactive sites includes a bead and multiple copies of a capture agent capable of specifically binding two or more distinct target analytes.
FIG. 1B schematically depicts a decoding table that includes several entries containing information about target analytes, which specifically bind to individual reactive sites of the bead array. The information about target analytes includes their identity, such as name, database ID and/or sequence and their molecular weights, mass-to-charge ratios and/or time-of-flight values.

In an embodiment, as schematically depicted in FIG. 1A, the instant specification describes a microarray, i.e. a bead array that includes a first reactive site 102 and a second reactive site 103. The first reactive site includes multiple copies of a first capture agent 112 bound to a first bead 111. The first capture agent 112 is configured to specifically bind a first target 121 and a second target 122. Both the first target and the second target are proteinaceous compounds containing an epitope 128, which is specifically recognized by the first capture agent. The molecular weight of the first target and the molecular weight of the second target are less than 5000 Daltons (Da). The molecular weight of the first target is different from the molecular weight of the second target. The molecular weight of the first target may differ from the molecular weight of the second target by less than 1 Da or by as much as several thousand Da. In an embodiment, a difference between the molecular weight of the first target and the molecular weight of the second target is greater than 5 Da. For example, the molecular weight difference between the first target and the second target may be greater than 10 Da, greater than 20 Da, greater than 50 Da, greater than 100 Da, greater than 200 Da, greater than 500 Da or greater than 1,000 Da. The second reactive site includes multiple copies of a second capture agent 114 bound to a second bead 113. The second capture agent is different from the first capture agent and configured to specifically bind a first target 123, a second target 124 and a third target 125. The capture agent of the second reactive site specifically recognizes an epitope 129, which is not recognized by the capture agent of the first reactive site. Each of the three targets 123, 124 and 125 has a distinct molecular weight Each of the three targets 123, 124 and 125 contains the epitope 129. The first and the second beads may be manufactured from a biocompatible material, such as glass, polystyrene, polypropylene, other types of polymers, agarose, cellulose, other types of hydrogels or a composite material. Each of the first and the second capture agents may be a monoclonal antibody, a polyclonal antibody, an antibody fragment, a single domain antibody, an aptamer, a SOMAmer® reagent, an affimer, a protein, a polypeptide, a receptor, a ligand, an enzyme, an enzyme substrate, an enzyme inhibitor or any other compound capable of affinity binding. For example, monoclonal or polyclonal antibodies may be selected to recognize a particular epitope such that an antibody conjugated to the first bead recognizes a different epitope than an antibody conjugated to the second bead.

In an embodiment, the first and the second beads and the first and the second capture agents are unlabeled, that is they do not comprise a detectable label. For example, both the beads and the capture agents may lack optical labels and mass tags. Furthermore, the first and the second beads may also lack positional encoding. Microarrays, in which the reactive sites lack positional encoding, do not allow identification of a capture agent based on a location of the reactive site.

Preferably, the amounts of the capture agents present on the first and the second beads are sufficient to enable binding of at least 100 attomoles of each target to their respective reactive sites. Depending upon the specific properties of the bead and the nature of the capture reagent, each of the reactive sites may have the capacity to bind more than 1 picomole or even more than 10 picomoles of their respective target.

The microarray may further include at least one replicate of at least one reactive site. For example, a replicate of the first reactive site schematically depicted in FIG. 1A may include a bead and a bead-linked capture agent that is chemically indistinguishable from the capture agent of the first reactive site. The microarray may contain between 1 and 100 replicates of a particular reactive site. For certain analytical applications it may be preferable that a microarray contains a relatively low number of replicates of a particular reactive site. For example, a microarray may contain fewer than 20, fewer than 15, fewer than 10 or fewer than 5 replicates of a particular reactive site. In fact, it is often sufficient to provide 1, 2, 3 or 4 replicates of a particular reactive site. In one aspect, having a low number of replicates of a particular reactive site may help ensure that a low-abundance analyte does not become overly diluted among many identical reactive sites, which would lead to a decrease in the intensity of a signal acquired from an individual reactive site. In another aspect, having a low number of replicate reactive sites may help lower the cost of the microarray manufacturing by reducing the amount of reagents, e.g. antibodies needed to make such microarray. In yet another aspect, having a low number of replicate reactive sites may help increase the multiplexing capability of a particular bead-based assay because a greater number of non-replicate reactive sites may be combined in a smaller reaction volume and subsequently analyzed on a solid support. It is noted that the methods and compositions disclosed in the instant specification enable highly efficient handling and analysis of individual beads and minimize the probability of losing beads throughout the microarray processing steps. The methods and compositions disclosed in the instant specification may be utilized to prevent losing even a single bead throughout the microarray processing steps and allow the end-user to analyze every bead within the microarray. The microarray handling procedures described in this specification make it possible to assemble a microarray in which at least some reactive sites are unique, i.e. have no replicates within the microarray. This may lead to increased detection sensitivity for many low abundance analytes.

In an embodiment, as schematically depicted in FIG. 1B, the microarray further includes a decoding table 130. The decoding table includes information about identities and molecular weights of targets that specifically bind to individual reactive sites of the microarray. For example, an entry 131, which is associated with the first reactive site and schematically depicted as "REACTIVE SITE 1", contains information about an identity and a molecular weight of the first target that specifically binds to the first reactive site, schematically depicted as "TARGET 1-1" and "VALUE 1-1" in columns 132 and 133 of the decoding table, respectively. The entry 131 further contains information about an identity and a molecular weight of the second target that specifically binds to the first reactive site, schematically depicted as "TARGET 1-2" and "VALUE 1-2", respectively. Likewise, an entry associated with the second reactive site, schematically depicted as "REACTIVE SITE 2", contains information about an identity and a molecular weight of each of the three distinct targets that specifically bind to the second reactive site.

If the target is a protein or has been derived from a protein, for example via enzymatic digestion of a protein, the information about an identity of the target may be one or more of the following: a name of the protein, an identifier of the protein, an accession number of the protein in a database, an amino acid composition of the protein, an amino acid composition of a region within the protein and an amino acid composition of a site within the protein. More generally, the information about an identity of a target may include one or more of the following: the name of the target, its chemical composition, its structural formula, etc. The information about a molecular weight of a target may be a value derived from the molecular weight of the target. Specifically, it may be one or more of the following: the molecular weight of the target, a mass-to-charge (m/z) ratio of the target, a time-of-flight (TOF) value of the target. It may also be another quantitative value that may be measured by mass spectrometry, such as the m/z ratio or the TOF value of: (1) a singly- or a multiply-charged form of the target, (2) a hydrogen adduct, ammonium adduct, sodium adduct, potassium adduct or other adduct of the target, (3) a target that underwent a loss of water, ammonia or other modification resulting in a decrease in its molecular weight, etc, (4) a target that underwent oxidation or other modification resulting in an increase in its molecular weight, etc. The decoding table may optionally also contain information about an identity of the corresponding capture agent. For example if the capture agent is an antibody, the decoding table may contain information about a sequence of the epitope recognized by the antibody, a manufacturer of the antibody, a catalog number of the antibody, etc. The data included in the decoding table may be stored in the printed medium, e.g. printed on a sheet of paper; alternatively it may be stored in the electronic medium, e.g. in a computer memory, on a removable memory device such as a USB memory card, in a cloud-based storage, etc. The data included in the decoding table may be also available via other means, e.g. posted on a website or sent and received by electronic communication, e.g. electronic mail or text messaging. Alternatively, the data included in the decoding table may be generated on-demand by a software program or another form of a computer algorithm.

Providing the decoding table enables identification of a target analyte based on the molecular weight (MW) or other properties of the target analyte, which may be measured by mass spectrometry, such as the mass over charge (m/z) ratio of the target analyte or the time-of-flight (TOF) value of the target analyte. In an embodiment, a single value derived from a molecular weight of a target is unambiguously associated with an identity of the target and therefore sufficient to unambiguously identify the target within the microarray. In an embodiment, the value derived from the molecular weight of the target is a value derived from the molecular weight of a non-fragmented form of the target. In other words, fragmentation of the target by tandem mass spectrometry is not required in order to determine the identity of the target. Furthermore, because the microarrays of the instant disclosure do not use liquid chromatography (LC) separations, key analytical parameters associated with LC measurements, such as analyte retention times do not need to be included in the decoding table.

It is not necessary for the microarray decoding table to contain information about the identity and the molecular weight of every distinct target that may specifically bind to a particular reactive site. In other words, the quantity of distinct targets that may specifically bind to a particular reactive site may be greater than the quantity of distinct targets, for which information about the identity and the molecular weight is available in the decoding table. For example, in reference to FIGS. 1A and 1B, the first reactive site 102 may specifically bind more than 2 distinct targets while the second reactive site 103 may specifically bind more than 3 distinct targets. The quantity of distinct targets, for which information about the identity and the molecular weight is available in the microarray decoding table, should be sufficient to allow unambiguous identification of a particular target, a particular group of targets or a particular reactive site within the microarray. In an embodiment, the decoding table contains the identity and molecular weight information for 2, 3, 4, 5, 6, 7, 8, 9, 10, 11 or 12 distinct targets, which may specifically bind to a particular reactive site. In an embodiment, the information about molecular weights of distinct targets, which may specifically bind to a particular reactive site, contains 2, 3, 4, 5, 6, 7, 8, 9, 10, 11 or 12 distinct values. In certain cases, the molecular weight of a target within a microarray may be sufficiently unique to allow unambiguous identification of the target based on a single measured MW, m/z or TOF value, which is schematically depicted as "REACTIVE SITE N", "TARGET N" and "VALUE N" in FIG. 1B.

In certain cases, the microarray decoding table may contain an entry for a particular reactive site, in which the quantity of targets, for which the molecular weight information is provided, is different from the quantity of targets, for which the identity information is provided. For example, the quantity of targets, for which the molecular weight information is provided, may be greater than the quantity of targets, for which the identity information is provided. Such case is schematically depicted in FIG. 1B as an entry labeled "REACTIVE SITE 3", in which the identity information is provided for a single target, depicted as "TARGET 3", yet the molecular weight information is provided for two distinct targets, depicted as "VALUE 3-1" and "VALUE 3-2". This may occur, for example, when a particular reactive site is capable of specifically binding a target, the identity of which is not known. Alternatively, the microarray manufacturer may choose not to disclose the identity of every target, for which the molecular weight information is provided in the decoding table.

The disclosed type of microarrays enables unambiguous identification of a target not only in a case when the molecular weight of a target is unique, but also in a case where the molecular weight of the target is not unique, i.e. two or more distinct targets within the microarray have identical or very similar molecular weights, which may not resolved by mass spectrometry. For example, in reference to FIG. 1A, the molecular weight of target 122, which specifically binds to the first reactive site 102, may be very close or identical to the molecular weight of target 125, which specifically binds to the second reactive site 103. If two distinct analytes have identical or very similar molecular weights they may not be distinguished by MALDI TOF mass spectrometry, although in some cases they may be distinguished by tandem mass spectrometry, e.g. MALDI TOF-TOF MS or by other types of mass spectrometry. It is also possible that a single target is capable of specifically binding to two or more distinct reactive sites within a microarray. For example, target 121 schematically depicted in FIG. 1A, which specifically binds to the first reactive site 102, may also specifically bind to the second reactive site 103. In such cases, a combination of molecular weights, m/z values or TOF values of two, three, four, five or an even greater number of distinct targets, which be may captured by a single reactive site of the microarray and detected together in a single mass spectrum, a so-called spectral signature will be sufficiently unique to enable unambiguous identification of the corresponding target(s) by mass spectrometry. The advantages of using two or a greater number of values to determine the identity of a particular target analyte and/or a particular reactive site may include greater confidence in the analyte identification and a higher degree of multiplexing for microarray-based analytical methods.

The disclosed type of microarrays is also suitable for analytical applications where the number of distinct targets captured by a same reactive site varies between different samples, e.g. different cell lines or a cell line that has been treated with different chemical compounds.

It was previously noted that the disclosed microarray encoding system may not require fragmentation or sequencing of a target analyte by mass spectrometry in order to identify the target analyte within the microarray. Nevertheless, analyte sequencing by mass spectrometry, e.g. by tandem mass spectrometry may be optionally performed for some or all of the target analytes present in the microarray, either to increase the confidence in the analyte identification or for purposes other than the analyte identification. For example, peptides may be analyzed by tandem mass spectrometry to determine the location of a post-translational modification within the peptide sequence.

Sequencing by mass spectrometry may be also used specifically for the purpose of identifying individual target analytes captured by a reactive site of the microarray. In such case, information about molecular weights and identities of the target analytes that is contained in the decoding table may be redundant and accordingly, the decoding table may not need to be supplied with the microarray. The microarray is decoded using MS-MS sequencing of individual target analytes captured by the microarray. One potential benefit of such approach is the possibility of discovering and identifying novel analytes that bind to the reactive sites of the microarray. However, this would require access to a more advanced MS instrument that is capable of performing MS-MS (MS2) analysis.

Sequencing by mass spectrometry may be also used for quantitative profiling of protein abundance changes in multiple samples using chemical labeling methods such as tandem mass tags (TMT) and isobaric tags for relative and absolute quantification (iTRAQ). Experimental examples included in this specification describe large diameter, high binding capacity magnetic agarose beads that are suitable for performing TMT and iTRAQ based protein quantification studies.

In an embodiment, a microarray of the instant disclosure includes multiple distinct reactive sites and a microarray decoding means, e.g. a microarray decoding table. Each of the reactive sites of such microarray is configured to specifically bind between 1 and 30 distinct targets, each target having a distinct molecular weight. Each of the reactive sites includes a bead and a capture agent associated with the bead. Each of the reactive sites is associated with a combination that contains between 1 and 30 distinct values, each of the values being derived from a molecular weight of a target that specifically binds to the corresponding reactive site. A combination associated with a particular reactive site serves as a code that enables identification of a target analyte using a measured molecular weight of the target analyte or an equivalent parameter, e.g. an m/z or a TOF value. Such combination may be a part of a microarray decoding table, which includes information about: (1) an identity and (2) a molecular weight of each of the targets. The decoding table may further include information about a quantity of distinct targets that may specifically bind to a particular reactive site. It may also include information about abundance of individual distinct targets in a biological sample, such as a biofluid or a cell lysate. The abundance information may be provided in a quantitative or a qualitative form. For example, the decoding table may contain a statement that certain peptide analytes are either not present or not detectable in a sample that is prepared from a particular cell line.

The microarrays of the instant disclosure may include between 2 and 100 distinct reactive sites. Alternatively, the microarrays of the instant disclosure may include more than 100 distinct reactive sites. Experimental examples of microarrays featuring multiple reactive sites are provided in this specification.

The microarrays of the instant disclosure may be configured to specifically bind between 2 and 100 distinct targets, each of the distinct targets having a distinct molecular weight. Alternatively, the microarrays of the instant disclosure may be configured to specifically bind between 100 and 500 distinct targets. Alternatively, the microarrays of the instant disclosure may be configured to specifically bind more than 500 distinct targets. The distinct targets may be derived from a single protein or from multiple distinct proteins. For example, a microarray may contain distinct capture agents, which specifically recognize and bind distinct proteolytic fragments of a naturally occurring precursor protein. The number of distinct proteolytic fragments of such precursor protein, which are recognized by the capture agents included in the microarray, may be 2, 3, 4, 5, 6, 7, 8, 9, 10 or greater than 10. Binding proteolytic fragments that are derived from various regions of a same precursor protein enables analysis of a substantial portion of the protein primary sequence, up to a complete sequence of the protein. Specifically, a microarray may contain distinct capture agents that bind distinct proteolytic fragments of a precursor protein, which collectively account for more than 5%, more than 10%, more than 20%, more than 30%, more than 40%, more than 50%, more than 60%, more than 70%, more than 80%, more than 90%, more than 95% or 100% of the primary sequence length of the protein. Such distinct capture agents are associated with distinct beads and therefore the distinct proteolytic fragments are captured by distinct reactive sites. Several examples of microarrays capable of binding distinct peptides derived from a same protein are provided in this specification.

The microarrays of the instant disclosure may be configured to perform analysis of fewer than 100 distinct targets, between 100 and 1,000 distinct targets or more than 1,000 distinct targets. The number of distinct targets that may be analyzed using the microarrays of the instant disclosure is determined by several factors including chemical composition of the individual targets, spectral resolution of the mass spectrometer and the detection mass range of the mass spectrometer. For example, for proteolytic peptides measured in the linear mode by MALDI TOF MS, the detection mass range may be set between approximately 800 Da and 8,000 Da. If molecular weights of the individual proteolytic peptides are spaced apart by about 5 Da, which is well within the spectral resolution capability of the modern MALDI TOF MS instruments, more than 1,000 distinct target analytes may be measured and unambiguously identified within such microarray.

The microarrays of the instant disclosure may be configured for binding multiple distinct targets, each of the distinct targets having a molecular weight that is greater than 700 Da and lower than 30,000 Da. The microarrays of the instant disclosure may be also configured for binding targets that have a molecular weight lower than 700 Da or greater than 30,000 Da. Experimental examples of microarrays capable of binding targets having molecular weights below 1,000 Da, between 1,000-10,000 Da, and greater than 10,000 Da are provided in this specification.

The microarrays of the instant disclosure may be configured to perform binding of multiple targets derived from a region of a protein that is adjacent to its C-terminus. To achieve this, an antibody may be selected to recognize an epitope located sufficiently close to the C-terminus in the protein primary sequence, e.g. less than 3, less than 5, less than 7, less than 10, less than 15, less than 20 or less than 25 amino acids from the protein C-terminus. Such microarrays may be used to detect protein heterogeneity, proteolytic degradation and/or protein modifications in the C-terminal region, among other effects.

The microarrays of the instant disclosure may be configured to perform binding of multiple targets derived from a region of a protein that is adjacent to the N-terminus of the protein. To achieve this, an antibody may be designed to recognize an epitope located sufficiently close to the protein N-terminus in the primary sequence, e.g. less than 3, less than 5, less than 7, less than 10, less than 15, less than 20 or less than 25 amino acids from the protein N-terminus. Such microarrays may be used to detect removal of the initiator Methionine and/or acetylation of the protein N-terminus, among other effects.

In an embodiment, the microarrays of the instant disclosure are configured for binding multiple distinct targets and include a decoding table that contains information about a fragmentation pattern of at least one of the distinct targets. The information about a fragmentation pattern of a particular target may be used to confirm an identity of the target. Experimental examples of microarrays that include a decoding table containing information about a fragmentation pattern of a target are provided in this specification.

The microarrays of the instant disclosure may include one or several reactive sites that lack positional, optical and mass tag encoding. In an embodiment, all reactive sites of a microarray lack positional, optical and mass tag encoding. Furthermore, unlike multiplexed sandwich immunoassays, the microarrays of the instant disclosure include only a single (capture) antibody per target analyte and do not require and do not include two distinct antibodies (capture and detection) per target analyte.

In an embodiment, the instant specification discloses a microarray that includes at least two distinct reactive sites and a decoding table. Each of the distinct reactive sites is capable of specifically binding at least one target. The decoding table contains information about an identity and a molecular weight of the targets that specifically bind to each of the distinct reactive sites and also information about an abundance of at least one of the targets in a sample. The decoding table may also optionally include a description of the sample, for which the target abundance data is provided.

Providing information about abundance of a target in a sample may help increase confidence in identification of the target by mass spectrometry after reacting the microarray with the sample.

The abundance information for a particular target may be provided in various forms. In an embodiment, the abundance information is provided as information about possible presence of the target in a sample, i.e. a particular target may be expected to be either present or absent in the sample. For example, a protein of mouse origin is not expected to be present in a sample derived from a human cell line. In another example, it may be known that a particular protein or a protein isoform is not expressed in a particular cell line, a particular organ or a particular tissue type and therefore its abundance in such sample will be zero. In an embodiment, the abundance information is provided as information about relative abundance of two or more targets in a sample. For example, two isoforms of a particular precursor protein may be expected to be present in a certain ratio, or at least one of the isoforms may be expected to be more abundant than the other. In another example, two PTM sites of a particular precursor protein may be expected to be present in a certain ratio, in which one site is modified, e.g. phosphorylated to a greater extent than the other. In an embodiment, the abundance information is provided in quantitative form. For example, information about abundance of a particular protein in serum or plasma may be known, at least approximately and expressed as the range of concentrations, e.g. mg/ml, µg/ml, ng/ml or pg/ml. In another example, an approximate intensity of a mass spec signal expected from a particular analyte may be provided.

The description of the sample, for which the target abundance data is provided, may include one or more of the following: the sample origin, e.g. a particular cell line, tissue, biofluid, etc; the sample treatment conditions, such as exposure of a cell line to a particular chemical compound; the sample processing history, e.g. the use of a particular digestive enzyme.

Several non-limiting examples of distinct target analytes that specifically bind to distinct reactive sites of a microarray are provided below and further described in the EXAMPLES section of the specification.

Peptide isoforms: these are peptides that have closely related but not identical amino acid sequences. The sequence differences may include amino acid additions, amino acid deletions, amino acid substitutions and amino acid modifications. The amino acid modifications may be post-translational modifications (PTMs), such as phosphorylation, acetylation, methylation, ubiquitination, glycosylation, etc. A single peptide sequence may contain more than one PTM site and more than one PTM type. For example, protein phosphorylation may occur on multiple neighboring sites within a single peptide sequence.

Peptides with different chemical modifications: a chemical modification of a peptide usually involves covalent attachment of one or more chemical groups to the peptide, either to a side-chain of an amino acid or to the peptide N- or C-terminal group. A large number of reagents capable of modifying peptides are known. For example, a peptide may be covalently modified with a compound containing an N-hydroxysuccinimide (NHS) ester or an imidoester, which target primary amines of lysine side-chains and the peptide N-terminus. Specifically, peptides may be differentially labeled with fluorescent dyes, such as cyanine dyes CY®3 and CY®5, coumarin or coumarin derivatives.

Peptides containing a different number of chemical modifications within an otherwise identical amino acid sequence: for example, a peptide may be chemically modified at the N-terminal amine and also at lysine side chain amine(s). Thus, a peptide with two lysine residues may contain 0, 1, 2 or 3 chemically modified amines.

An endogenous peptide and an internal standard: an internal standard is usually spiked, i.e. added into a sample, which already contains an endogenous peptide. The internal standard may be a synthetic peptide, which has a sequence that is distinct from the sequence of the endogenous peptide.

Proteolytic peptides containing missed cleavage sites: digestion of a precursor protein by a digestive enzyme, such as trypsin, chymotrypsin, endoproteinase GluC, LysC, LysN, Arg-C, pepsin, elastase, etc may produce multiple peptides containing 0, 1, 2, 3, 4, 5, 6 or a greater number of missed cleavages. Such peptides may have a same epitope but different length and consequently different molecular weight. Furthermore, some digestive enzymes may exhibit non-specific activity, for example certain preparations of trypsin may additionally exhibit chymotrypsin activity. In such scenario a proteolytic peptide may contain a cleavage site that is not typical or expected for the corresponding digestive enzyme.

Peptides produced by non-enzymatic hydrolysis of a peptide bond: certain types of peptide bonds have inherently low stability and may undergo hydrolysis even in the absence of a digestive enzyme. These include hydrolysis of methionine-containing peptide bonds in the presence of cyanogen bromide, hydrolysis of an aspartic acid-proline peptide bond in the presence of formic acid and hydrolysis of an asparagine-glycine peptide bond in the presence of hydroxylamine. A partial hydrolysis of a peptide bond will result in appearance of two or more distinct peptides of different length.

Peptides originating from different species: certain biological techniques, such as production of tumor xenografts coupled with proteolytic digestion may generate a mixture of peptides that originate from different species, e.g. human and mouse. Such peptides may have a same epitope but differ in the amino acid composition outside the epitope.

Peptides derived from proteins that share an identical or similar sequence within an epitope, which is recognized by a capture agent of the reactive site. Such proteins may be constituents of a same biological pathway or distinct biological pathways. In the latter case, a single microarray reactive site may be configured to specifically bind peptides derived from proteins that are constituents of 2, 3, 4, 5, 6, 7, 8, 9, 10 or a greater number of distinct biological pathways. Thus, a single microarray reactive site may be configured to probe changes in 2, 3, 4, 5, 6, 7, 8, 9, 10 or a greater number of distinct biological pathways.

Figure 2A:
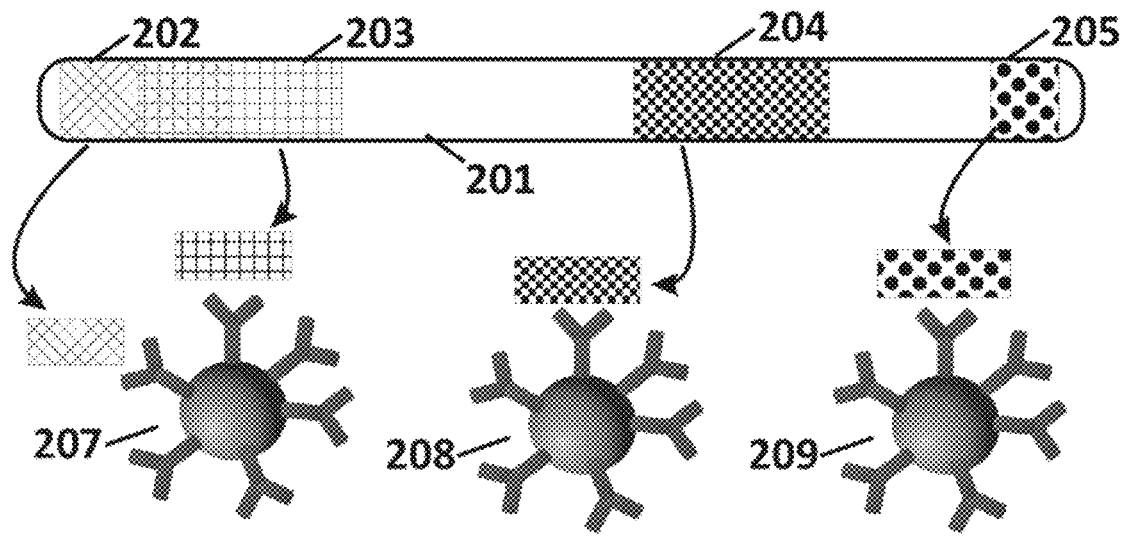
FIG. 2A schematically depicts a method for performing affinity binding, in which distinct proteolytic fragments of a precursor protein are captured on distinct reactive sites of a bead array.
Figure 2B:
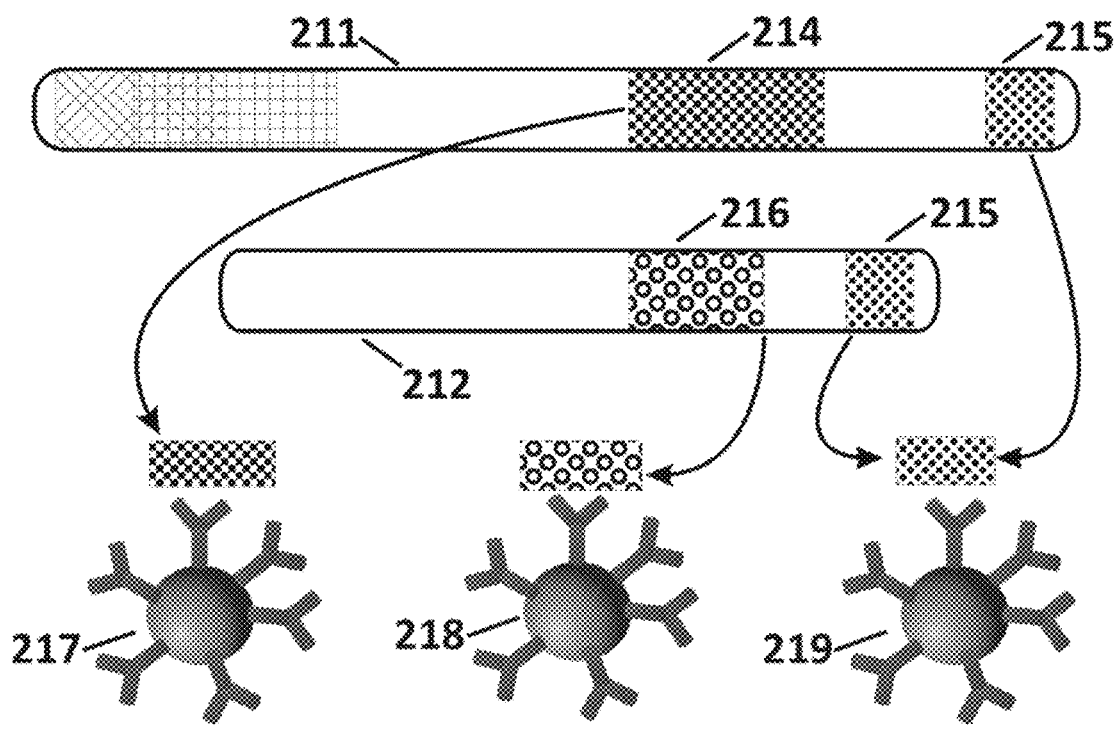
FIG. 2B schematically depicts a method for performing affinity binding, in which proteolytic fragments derived from distinct precursor proteins are captured on a same reactive site of a bead array.

FIGS. 2A-2B schematically depict some examples of microarrays and methods of performing affinity binding using microarrays. In reference to FIG. 2A, a microarray, i.e. a bead array may contain distinct capture agents that are associated with distinct beads 207, 208 and 209. The distinct capture agents specifically recognize distinct epitopes that are present in a sequence of a naturally occurring protein 201. If the epitopes are preserved after proteolytic digestion, the distinct reactive sites will also specifically recognize and specifically bind distinct proteolytic fragments 202, 203, 204 and 205, which contain the corresponding epitopes. The microarray may contain multiple distinct capture agents that specifically recognize multiple distinct proteolytic fragments, which collectively account for more than 10%, more than 20%, more than 30%, more than 40%, more than 50%, more than 60%, more than 70%, more than 80%, more than 90%, more than 95%, or 100% of a sequence length of the protein. For example, two proteolytic fragments of a protein collectively account for more than 20% of a sequence length of the protein if the proteolytic fragments are non-overlapping, each proteolytic fragment contains more than 10 amino acids and the entire protein contains less than 100 amino acids.

If overlapping proteolytic fragments 202 and 203 contain the same epitope, which may occur for example due to incomplete enzymatic digestion, they will be recognized by the same capture agent and captured by the same reactive site 207, as schematically depicted in FIG. 2A.

In reference to FIG. 2B, it is possible that proteolytic digestion of two distinct proteins 211 and 212 will generate identical fragments 215, which will be captured by a same reactive site 219 of the bead array. Measuring the abundance of the fragment 215 will provide information about the abundance of both precursor proteins 211 and 212 but will not provide information about the abundance of the individual proteins. Including additional reactive sites 217 and 218, which specifically capture proteolytic fragments 214 and 216, derived from the proteins 211 and 212, respectively, will enable protein-specific quantification. Alternatively, it is possible that the fragments 215 derived from the proteins 211 and 212 have a common epitope but different molecular weights due to differences in their amino acid composition outside of the epitope. In such case, the fragments will be distinguished by mass spectrometry even when captured on a single reactive site.

The distinct capture agents in the microarray may individually recognize distinct epitopes within a proteinaceous compound that has a molecular weight less than 5000 Da.

The epitope recognized by a capture agent of the microarray may be a naturally occurring sequence that is present in a human protein and in a mouse protein, or more generally, in at least two proteins from different species. Accordingly, a reactive site of the microarray may bind proteolytic fragments that are derived from both human and mouse proteins. An example of such microarray is provided in the specification.

A microarray may be designed such that an epitope recognized by a capture agent of a first reactive site naturally occurs in a first protein and in a second protein while an epitope recognized by a capture agent of a second reactive site naturally occurs in the first protein but not in the second protein. An example of such microarray is provided in the specification.

A microarray may be designed such that epitopes recognized by capture agents of a first and a second reactive sites lack proteolytic cleavage sites that are recognized by trypsin and chymotrypsin. Trypsin usually recognizes proteolytic cleavage sites containing lysine or arginine, except when they are followed by proline or are adjacent to a phosphorylated amino acid, such as phosphoserine, phosphothreonine, phosphotyrosine. In some cases, trypsin may not recognize sites containing Lys-Lys, Arg-Arg, Lys-Arg or Arg-Lys sequences. Chymotrypsin usually recognizes sites containing a large hydrophobic amino acid such as tyrosine, tryptophan, and phenylalanine, although it may also recognize sites containing leucine, isoleucine and methionine. Such microarray may be useful for profiling samples produced by enzymatic digestion using either trypsin or chymotrypsin. An example of such microarray is provided in the specification.

A microarray may be designed such that an epitope recognized by a capture agent of a first reactive site lacks a proteolytic cleavage site that is recognized by trypsin while an epitope recognized by a capture agent of a second reactive site contains such proteolytic cleavage site. Such microarray may be useful for profiling samples produced by enzymatic digestion using either trypsin or another protease. An example of such microarray is provided in the specification.

A microarray may be designed such that epitopes recognized by capture agents of a first and a second reactive sites lack proteolytic cleavage sites that are recognized by at least two digestive enzymes, e.g. by at least two of trypsin, chymotrypsin, pepsin, elastase, thermolysin, endoproteinase Arg-C, endoproteinase Glu-C and endoproteinase Asp-N. An example of such microarray is provided in the specification.

A microarray may be designed such that a capture agent of a first reactive site specifically recognizes an epitope that lacks a PTM and specifically binds a first target and a second target, both of which contain the epitope, yet only one of the two targets contains the PTM, which is located outside of the epitope. An example of such microarray is provided in the specification.

A microarray may be designed such that a capture agent of a first reactive site specifically recognizes an epitope containing a first PTM, e.g. phosphorylation and specifically binds a first target and a second target, both of which contain the epitope while at least one of the targets also contains a second PTM, e.g. acetylation, methylation, glycosylation, ubiquitination or sumoylation, which is located outside of the epitope. A site of the first PTM may be separated from a site of the second PTM by less than 10 amino acids. An example of such microarray is provided in the specification.

A microarray may be designed such that a capture agent of a first reactive site specifically recognizes an epitope containing at least 2 PTMs and specifically binds a first target and a second target, at least one of which further contains an additional PTM, which is located outside of the epitope. An example of such microarray is provided in the specification.

A microarray may be designed such that distinct reactive sites of the microarray specifically bind at least 3 distinct proteolytic fragments of a naturally occurring protein. In an embodiment, each distinct fragment contains at least one PTM. An example of such microarray is provided in the specification.

A microarray may include capture agents that specifically recognize their corresponding epitopes in western blot, ELISA, flow cytometry, immunohistochemistry, immunoprecipitation or immunofluorescence assay. An example of such microarray is provided in the specification.

A microarray may include a capture agent that specifically binds two distinct targets: a first target, which is detectable by linear mode MALDI TOF MS, but not by reflector mode MALDI TOF MS, and a second target, which is detectable by reflector mode MALDI TOF MS. Targets detectable by linear mode MALDI TOF MS include compounds that are labile, e.g. phosphopeptides, or have high molecular weight, e.g. greater than 10 kDa. Goat Anti-Aconitase 2 antibody described in detail in Example 14 recognizes both intact ACO2 protein (MW 85,425 Da, detectable by linear mode MALDI TOF MS using sinapinic acid as a matrix) and its proteolytic fragment, which includes amino acids 541 through 555 (MW 4781.1 Da, detectable by reflector mode MALDI TOF MS using α-Cyano-4-hydroxycinnamic acid as a matrix).

A microarray may include a capture agent that specifically binds two distinct targets, which require different matrices for detection by MALDI MS. Examples of such different matrices include α-Cyano-4-hydroxycinnamic acid (CHCA) and 2,5-Dihydroxybenzoic acid (DHB), CHCA and sinapinic acid (SA), CHCA and 2',6'-Dihydroxyacetophenone (DHAP) and other combinations. An example of such capture agent is Goat Anti-Aconitase 2 antibody described in the previous paragraph.

In an embodiment, two distinct targets do not comprise an isotopic label, i.e. the first target and the second target have similar isotope abundance. For example, both the first and the second targets may have natural isotope abundance with respect to every chemical element present in their structure. For carbon and nitrogen, the natural isotope abundance is known to be about 98.9% of $^{12}C$ and about 99.6% of $^{14}N$, respectively.

In an embodiment, two distinct targets have different isotope abundance, e.g. the first target, the second target or both the first target and the second target are isotope labeled. Isotope labeling of a peptide may be achieved by incorporating one or several stable isotopes, such as $^2H$, $^{13}C$, $^{15}N$ and $^{18}O$. Isotope labeling of a peptide may be also achieved by using radioactive isotopes. The presence of an isotope label in a single amino acid usually results in a mass shift of between 4 and 10 Da relative to an unlabeled version of the same amino acid.

It is noted that a mass difference between an unlabeled and an isotope-labeled forms of a proteolytic peptide in a typical bottom-up proteomic assay usually does not exceed 10 Da. In part, this is because the most common digestive enzyme, trypsin generally produces peptides containing a single Lysine or Arginine residue. The $^{13}C$, $^{15}N$ isotope-labeled versions of Lysine and Arginine differ from their unlabeled counterparts by 8 and 10 Da, respectively. Using other digestive enzymes, such as chymotrypsin may generate proteolytic peptides containing several Lysine and/or Arginine residues but may also produce peptides that do not contain these amino acids.

In an embodiment, the reactive site is being configured to enable the release of the first and the second targets from the bead in a form that is compatible with analysis of the first and the second targets by mass spectrometry. Throughout the present specification, the use of mass spectrometry is illustrated primarily using an example of Matrix Assisted Laser Desorption Ionization Time-of-Flight Mass Spectrometry (MALDI TOF MS). However, it is noted that numerous other methods of mass spectrometric analysis may be alternatively used, both with respect to the analyte ionization and the analyte detection. In particular, various methods of ElectroSpray Ionization MS (ESI MS) analysis may be used, including methods known as Laser Ablation ElectroSpray Ionization (LAESI) and Desorption ElectroSpray Ionization (DESI) MS.

In an embodiment, the first and the second targets are peptides and the analysis by mass spectrometry is performed by MALDI TOF MS in the linear mode. Advantages of measuring peptides in the linear mode compared to the reflector mode may include greater detection sensitivity and minimization of spectral contributions from the analyte fragmentation, such as in-source decay (ISD) and post-source decay (PSD). For example, many phosphopeptides are known to undergo extensive fragmentation inside a mass spectrometer when measured by MALDI TOF MS. However, spectral effects of their fragmentation are less pronounced in mass spectra acquired in the linear mode compared to mass spectra acquired in the reflector mode. For peptide analysis performed by MALDI TOF MS, the positive detection mode is more frequently used although the negative detection mode may be utilized as well. For analytes that have a molecular weight lower than approximately 10,000 Da, measurements by MALDI TOF MS may be performed in the reflector mode. In addition, measurements of certain analytes by MALDI TOF MS may be performed in the tandem (MS-MS) mode.

Mass over charge (m/z) ratio is one of the analyte properties that are commonly measured by mass spectrometry. Converting the measured m/z ratio into the analyte molecular weight (MW) is usually straightforward. For example, peptide analytes measured by MALDI TOF MS in the positive mode are often detected as single-charge protonated ions, in which the charge (z) is +1 and the mass (m) is equal to the molecular weight of the peptide analyte plus the mass of a proton. Therefore, mass spectrometry may be used to determine molecular weight of a measured analyte. Molecular weight, also termed molecular mass, is usually reported in atomic mass units (amu) or Daltons (Da). The presence of stable isotopes, such as $^{13}C$ and $^{15}N$ in the analyte structure leads to appearance of multiple peaks in the analyte mass spectra, which are separated by about 1 m/z unit. Such multiple peaks are known as the isotopic envelope. Due to the presence of the isotopic envelope, the analyte molecular mass measured by mass spectrometry may be reported either as monoisotopic mass or as average mass.

The microarrays disclosed in this specification may be described as target-encoded bead arrays, in which an identity of a target analyte bound to a particular bead may be determined by direct mass spectrometric measurement of that target analyte. A target-encoded bead array may not require positional, optical or mass tag encoding of individual beads. Furthermore, a target-encoded bead array may not require mass spectrometric analysis of the capture agents. Consequently, a capture agent may remain bound to a bead even after the corresponding target analyte has been released from the bead. Retaining the capture agent on the bead after the release of the target analyte from the bead may help obtain better quality mass spectra, e.g. mass spectra with a lower background and a stronger analyte signal. Alternatively, the capture agent may be released from a bead in a form that is not necessarily compatible with analysis by mass spectrometry, e.g. the molecular weight of the capture agent may be outside of a mass detection range of the mass spectrometer.

A target-encoded bead array is decoded after the binding of a target analyte to its respective capture agent has occurred, e.g. after the bead array has been exposed to a sample and preferably after an unreacted portion of the sample has been removed. It is noted that analysis by mass spectrometry comprises measurement of signal intensity at multiple m/z positions (multiple mass channels); therefore a single mass spectrometric measurement may provide sufficient data to determine both an identity of a particular target analyte and its abundance in the sample.

It is noted that successful identification of a target analyte in a target-encoded bead array is dependent upon the presence of a sufficient amount of the target analyte in a sample. If the amount of the target analyte in the sample is below the detection limit the target analyte will not be detected or identified. Nevertheless, such negative result provides valuable information because it reveals that the particular target analyte is either absent in the sample or its abundance in the sample is below a certain threshold.

An exemplary method of fabricating a target-encoded bead array is disclosed below and described in greater detail in the EXAMPLES section of the specification. In an embodiment, the method includes the steps of: (1) selecting a capture agent that is capable of binding to a bead and when bound to the bead is capable of binding at least a first target and a second target that have different molecular weights and (2) recording a decoding table, the decoding table containing information about an identity of the first target, a value derived from the molecular weight of the first target and a value derived from the molecular weight of the second target.

Step 1: selecting a capture agent. This step involves selecting and acquiring antibodies to be utilized in the bead array. An antibody may be selected for the purpose of profiling a specific biomarker, profiling a specific type of protein modification, profiling a specific biological or cellular pathway, profiling multiple cellular pathways, profiling molecular changes associated with a specific disease or a specific cellular condition, etc. An antibody may be selected to profile total protein abundance, alternatively an antibody may be selected to profile site-specific protein abundance, such as an extent of a protein post-translational modification (PTM) at a specific protein site. An antibody may be purchased from a commercial vendor or be custom-produced. An antibody may be monoclonal or polyclonal. An antibody may be raised in various host species, e.g. rabbit, mouse, goat, horse, chicken or it may be synthetically produced. Antibodies from different host species may be utilized within a same bead array. In an embodiment, the immunogen is a peptide. In an embodiment, the immunogen is a full-length protein or a biological cell. It is preferred that the epitope sequence or the sequence of an immunizing peptide for a particular antibody is known. However, it is also possible to utilize antibodies for which the epitope sequence or the sequence of an immunizing peptide is not known. An example of the latter is shown in the EXAMPLES section of the specification.

Obtaining an antibody from a commercial vendor may be advantageous because many commercially available antibodies are already provided with a list of applications for which these antibodies have been validated, e.g. western blot (WB), immunoprecipitation (IP), immunofluorescence (IF), immunohistochemistry (IHC), flow cytometry (FC), chromatin immunoprecipitation (ChIP), enzyme-linked immunosorbent assay (ELISA), sandwich immunoassays, etc. Such information may be valuable because it enables integration of quantitative analysis of a specific protein target by mass spectrometry with follow-up studies of the same protein target performed using the above-listed applications in cell cultures, tissues, biofluids and animal models.

One consideration when selecting an antibody with a known epitope is that the epitope should be preserved in the target analyte. Specifically, if a sample to be analyzed is produced by incubation of a protein with a digestive enzyme the epitope preferably should not contain a cleavage site of the digestive enzyme. For example, for samples produced by incubation with trypsin the epitope preferably should not contain an internal arginine or lysine. Likewise, for samples produced by incubation with Lys-C or Lys-N the epitope preferably should not contain an internal lysine. However, the above requirement is not absolute since incomplete digestion by a digestive enzyme may preserve the epitope even when a potential cleavage site is present within the epitope. In addition, certain protein modifications may alter the pattern of cleavage sites normally recognized by a digestive enzyme. For example, phosphorylation of a tyrosine adjacent to a lysine frequently results in a missed cleavage by trypsin. Another consideration for selecting an antibody with a known epitope is that a linear or continuous epitope is generally preferred for performing peptide immunoaffinity enrichment.

Overall, the total number of distinct capture agents, e.g. distinct antibodies selected for a particular bead array may be fewer than 10, between 10 and 30, between 30 and 100, between 100 and 500, between 500 and 1,000, between 1,000 and 10,000 or greater than 10,000. Multiple replicate beads may be provided for each capture agent, e.g. 2 beads, 3 beads, 5 beads, 10 beads or a greater number. For spherical beads that are approximately 300 µm in diameter, about 25 beads may be packed into 1 µL volume, about 2,500 beads may be packed into 100 µL volume and about 25,000 beads may be packed into 1 ml volume. A microwell plate with dimensions of a standard microscope slide, 25×75 mm may be used to array over 5,000 of 300 µm diameter beads. A microwell plate with dimensions of a standard microtiter plate, 86×128 mm may be used to array over 25,000 of 300 µm diameter beads.

Step 2: recording a decoding table. This step involves elucidating the identity of peptides that may bind to individual antibodies previously selected in Step 1. Specifically, for a peptide, which is expected to bind to a particular antibody, an amino acid sequence of the peptide including possible post-translational modifications (PTMs) and the peptide molecular weight are preferably elucidated. Such data may be generated by analyzing the known epitope sequence(s) for a particular antibody and subsequently determining the peptide amino acid composition outside the epitope(s) to account for different sample preparation conditions associated with a particular analytical workflow. For example, the peptide length and molecular weight may be affected by the selection of a digestive enzyme used to prepare the sample. The use of common proteomic techniques such as cysteine reduction and alkylation will also affect the amino acid sequence and molecular weight of the resulting peptides. Furthermore, the nature of the sample that is being analyzed may also contribute to the presence of different target analytes, for example mammalian cells cultured under conditions that cause elevated levels of protein phosphorylation are expected to produce peptides with greater numbers of phosphorylated sites.

An alternative method, which is also disclosed in the instant specification, involves experimental testing and validation of individual antibodies performed under defined conditions that can be subsequently documented. Such conditions may include the use of a certain digestive enzyme, use of a certain sample type, e.g. cell culture, use of a certain cell line, use of a certain method of mass spectrometry and use of a certain analytical technique, e.g. profiling of protein phosphorylation. In the disclosed method an individual antibody, which is preferably bound to a solid support, e.g. a bead, is exposed to a sample containing the target analyte (s) and an immunoaffinity capture reaction is performed. The target analyte(s) that bind to the antibody are subsequently released from the solid support and analyzed by mass spectrometry. The analysis by mass spectrometry may include determination of molecular weights of the individual target analytes, as well as determination of the amino acid sequence of the individual target analytes performed using known fragmentation techniques such as collision induced dissociation (CID), electron transfer dissociation (ETD), in source decay (ISD), post source decay (PSD), etc. The procedure disclosed above is then repeated for other antibodies within the bead array.

An exemplary method of analyzing a biological sample using a target-encoded bead array is disclosed below and described in greater detail in the EXAMPLES section of the specification. In an embodiment, the target-encoded bead array includes at least one reactive site and a decoding table. An example of a reactive site is an antibody bound to a bead. The bead-bound antibody is capable of binding at least two distinct target analytes with different MW: a first target analyte and a second target analyte. The decoding table includes information about the identity of the first target analyte, information about the MW, m/z ratio and/or TOF value of the first target analyte, optional information about the identity of the second target analyte and information about the MW, m/z ratio and/or TOF value of the second target analyte. Therefore, the decoding table contains sufficient information to enable identification of the first target analyte in a bead array based on the detection of two signals in a mass spectrum, which are associated with values derived from the MW of the first target analyte and the MW of the second target analyte. In some cases, detection of even a single signal in a mass spectrum may be sufficient to unambiguously identify the first target analyte. This may happen if the molecular weight of the first target analyte is sufficiently unique, that is no other target analytes captured by the bead array has the same or very similar molecular weight.

In an embodiment, the method of analyzing a biological sample using a target-encoded bead array includes the following steps: (1) contacting a reactive site of the bead array with a sample that contains or may contain the first target and the second target under conditions that allow binding of the first target and the second target to the reactive site; (2) after the contacting step, acquiring a mass spectrum from the reactive site such that a signal from the first target and a signal from the second target are either detectable or actually detected in the mass spectrum, (3) identifying the signal from the first target and the signal from the second target in the mass spectrum using the decoding table provided with the bead array and (4) measuring intensity of the signal from the first target and intensity of the signal from the second target.

Step 1: contacting the reactive site with a sample. This step may include performing an immunoaffinity purification (IAP) reaction and subsequently removing an unreacted portion of the sample from the reactive site. Various methods of performing bead-based IAP reactions are known in the art. For example, a suspension of beads may be simply mixed with an aqueous solution containing the sample and incubated for a specific amount of time.

Step 2: acquiring a mass spectrum. This step may include eluting the bound target analyte(s) from the bead onto a spot on a solid support, such as a MALDI target plate and using mass spectrometry to analyze the eluted analyte(s) localized within such spot. The bead may remain on the solid support; alternatively, the bead may be removed from the solid support prior to the measurement by mass spectrometry. When analysis by mass spectrometry involves the use of MALDI MS, the eluted analyte should be mixed with a MALDI matrix. The intensity of the ionization laser beam of a MALDI mass spectrometer should be selected such that a sufficiently strong signal from the eluted analyte(s) can be recorded, e.g. a signal is considered to be sufficiently strong if its signal-to-noise ratio is at least 3:1, preferably at least 10:1, more preferably at least 30:1, most preferably at least 100:1. The methods disclosed in the instant specification allow detection of analytes eluted from a single bead by MALDI TOF MS with a signal-to-noise ratio greater than 1000:1. It is noted that the intensity of the ionization laser beam may require an adjustment when multiple spots containing different analytes are measured.

Step 3: identifying the signal from the first target and the signal from the second target. In an embodiment, this step includes searching the acquired mass spectrum for a signal, e.g. a peak with an intensity above the background level and once such peak has been detected at a specific m/z value, searching the decoding table to find a target analyte associated with an m/z value that is identical or sufficiently close to the m/z value detected in the mass spectrum. This process is then repeated if other peaks are present in the mass spectrum. In some cases, identification of the target analyte may be accomplished by detecting a single peak in the mass spectrum. Alternatively, identification of the target analyte may be accomplished by detecting two or more peaks in the mass spectrum.

Step 4: measuring intensity of the signal from the first target and intensity of the signal from the second target. This step may be accomplished by using analytical software to determine intensity of the peak(s) detected in the mass spectrum. The signal intensity may be reported as the peak height, area under the peak or using other known formats.

Incubation of a sample with individual reactive sites of the microarray may result in non-specific binding of one or more compounds to the reactive site. Such compounds may be bound to the bead, alternatively they may be bound to the capture agent or bound to the linker, e.g. Protein A or Protein G. To alleviate the problem of non-specific binding, the decoding table may contain information about m/z values associated with such non-specifically bound compounds.

In an embodiment, the first target analyte and the second target analyte are peptides that have been differentially modified. For example, two peptides may be differentially modified at their N-termini, C-termini or both. The two peptides may be also differentially modified at specific amino acids, e.g. lysine, cysteine, aspartic acid, glutamic acid, arginine, histidine, etc. For the methods disclosed in the instant specification suitable peptide modifications include modifications with compounds that have differential isotope abundance as well as modifications with compounds that have same, e.g. natural isotope abundance.

In an embodiment, the first target analyte and the second target analyte are peptides that are not differentially modified. For example, the first target analyte may be an endogenous peptide produced by enzymatic digestion of a biological specimen and the second target analyte may be an internal standard peptide added to the enzymatically digested biological specimen containing the first target analyte. In this example, the first and the second target analytes may have same, e.g. natural isotope abundance but differ in their amino acid composition, the differences in the amino acid composition being a substitution, a modification, an addition or a deletion of at least one amino acid.

In an embodiment, a sample suitable for analysis by the microarrays of the instant disclosure is a digested biospecimen, such as a suspension or a pellet of cultured biological cells, a biological tissue, a biological fluid or a xenograft. The digestion may be performed using enzymatic or non-enzymatic compounds. Furthermore, the biospecimen may be subjected to cell lysis prior to performing the digestion reaction.

In certain applications however, the biological sample does not need to be lysed and/or digested prior to performing the affinity enrichment step. For example, unfractionated serum is known to contain a large number of circulating peptides. Another example is analysis of secreted peptides that are released from cultured cells into the cell culture medium.

The microarrays disclosed in the instant specification are suitable for profiling diverse types of protein PTMs such as phosphorylation, acetylation, methylation, glycosylation, ubiquitination, sumoylation and others. In an embodiment, a microarray reactive site contains an antibody or an aptamer that specifically binds to an epitope and every target that is specifically captured by the microarray reactive site contains the epitope. In an embodiment, the epitope contains fewer than 6 contiguous amino acids, fewer than 5 contiguous amino acids or fewer than 4 contiguous amino acids. In an embodiment, the epitope is discontinuous, that is, at least some of the amino acids, which are recognized by the corresponding antibody, are not adjacent to each other. In an embodiment, the epitope contains a first PTM and at least one of the targets contains a second PTM that is located outside of the epitope. In an embodiment, the epitope does not contain a PTM and at least one of the targets contains the PTM. In an embodiment, each target that binds to the microarray reactive site contains a protein site that is post-translationally modified in at least one target and lacks a PTM in at least one target. In an embodiment, individual targets captured by the microarray reactive site are derived from distinct proteins that are constituents of distinct biological pathways.

The present disclosure is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the present disclosure, and are not intended to limit the scope of the present disclosure nor are they intended to represent that the experiments below are all or the only experiments performed. Efforts have been made to ensure accuracy with respect to numbers used (e.g. amounts, temperature, volume, time etc.) but some experimental errors and deviations should be accounted for.

EXAMPLES

Materials and Equipment

N-Hydroxysuccinimide (NHS)-activated magnetic 6% agarose beads were custom manufactured by Cube Biotech (Plymouth Meeting, Pa.). The diameter of individual beads was between approximately 250 µm and 500 µm, as determined by optical microscopy. These polydisperse beads were further separated into fractions with narrower size distributions including fractions containing beads in the <280 µm, 280-355 µm, 355-375 µm, 355-400 µm, 375-400 µm, 375-420 µm, 400-420 µm, 400-450 µm and >450 µm diameter range. The bead fractionation was accomplished by manually passing the bead suspension through a series of polyester mesh filters (ELKO Filtering Co, LLC) until a desired size fraction was produced. The size fractionated beads were stored in pure isopropanol (Fisher Chemical, catalog No. A416-4) until further use.

For certain applications, magnetic agarose beads with varying degrees of agarose cross-linking were used. It was experimentally determined that beads with higher degree of agarose cross-linking when placed into wells of a 96-well multiwell plate filled with an aqueous medium were able to withstand rigorous shaking of the plate, e.g. at a speed of 800 RPM or greater for over 12 hours without individual beads breaking apart.

For certain applications, magnetic beads with the agarose content greater than 6% were used, e.g. the beads contained either 7.5% or 9% agarose. It was experimentally determined that beads with the agarose content greater than 6% generated stronger MS signals after binding and subsequent elution of various peptide analytes.

For certain applications, larger magnetic agarose beads were used, e.g. beads in the 700-790 µm, 790-910 µm and >910 µm diameter range.

For certain applications, smaller size magnetic agarose beads were used, e.g. beads in the 160-200 µm diameter range.

Indium Tin Oxide (ITO) surface coated glass microscope slides, catalog No. 237001 were from Bruker Daltonics (Billerica, Mass.). Individual slides have dimensions of 25 mm×75 mm×0.9 mm and are designed to be used with the MTP Slide Adapter II for MALDI imaging, available from Bruker Daltonics (catalog No. 235380).

Gold surface-coated glass microscope slides were from Fisher Scientific (catalog No. 12-550-59).

Silicone microwell gaskets, also known as SILICONE ISOLATORS™, were custom manufactured by Grace Bio-Labs (Bend, Oreg.) using a standard grade of polydimethylsiloxane (PDMS). Overall dimensions of a silicone gasket were 25 mm×75 mm×0.5 mm. Each gasket contained a square grid array of 26×88 microwells. An internal diameter of each microwell was 0.5 mm with adjacent microwells separated by a distance of 0.3 mm (a distance of 0.8 mm measured as center-to-center). An area of approximately 2.5 mm between peripheral wells and the edges of the gasket contained no wells.

For certain applications, silicone gaskets with smaller length and/or width were used, including 25 mm×73 mm×0.5 mm, 23 mm×75 mm×0.5 mm and 23 mm×73 mm×0.5 mm. A silicone gasket with a smaller width and/or length when affixed to a 25 mm×75 mm ITO glass slide forms a watertight seal that has a lower risk of breaking during manual handling because the fingers are less likely to inadvertently pull the gasket from the slide when the slide is being held from the edges.

PROPLATE® multi-well chambers in several configurations including 1, 2, 3, 4, 8, 16, 24 and 64 chambers were purchased from Grace Bio-Labs.

Protein A+G was purchased from Abcam (catalog No. ab52213). The product description posted on the manufacturer's website refers to Protein A+G as " . . . a genetically engineered fusion protein that combines the IgG binding profiles of both Protein A and Protein G".

Unless noted otherwise, consumables such as microcentrifuge tubes, pipette tips, weigh boats etc, were standard research grade. Unless noted otherwise, the reagents such as organic solvents, acids, salts, buffers, detergents, MALDI matrices etc, were standard research grade with a purity of 99% or higher and used as received from the manufacturer without further purification. Standard lab equipment included a microcentrifuge, a microplate centrifuge, magnetic tube racks, microtiter plate shaker, vortexer, etc.

Robotic liquid sprayer iMatrixSpray for depositing MALDI matrix solutions was purchased from Tardo GmbH (Subingen, Switzerland). The design and operation of iMatrixSpray are described in a recent publication: CHIMIA International Journal for Chemistry (2014), Volume 68(3), pp. 146-149.

Experimental Results

Some of the experiments performed using the compositions and methods disclosed in this application and the resulting experimental data are described below.

Example 1

Preparing Protein A+G Conjugated Magnetic Agarose Beads

Using the magnetic QuicPick device (Bio-Nobile, catalog No. 24001), between 100 and 125 of size-fractionated Cube Biotech PureCube MagBeads XXL NETS-activated beads in isopropanol were transferred to a 0.65 mL plastic microcentrifuge tube (Costar, catalog No. 3208) containing about 300 µL of isopropanol. The isopropanol was subsequently removed. About 640 µL of 1×PBS (Fisher Scientific, catalog No. BP24384) was added to the tube and the tube was rotated at room temperature for 5 minutes. 80 µg of recombinant Protein A+G in 1×PBS was added to the tube. Additional amount of 1×PBS was added until the tube was full. The tube was incubated on a tube rotator (Silent Shake Revolver from Crystal Industries, catalog No. HYQ-1130A) at low speed, 4° C. for 3 hours at minimum, usually overnight. The tube was removed from the rotator and centrifuged briefly for less than 2 seconds. The supernatant was removed. 20 µL of 10× Tris-Glycine buffer was added to quench the remaining reactive NETS groups. The tube was incubated on a tube rotator at low speed at room temperature for 30 minutes. The Tris-Glycine buffer was removed and replaced with 300 µL of 1×PBS. The beads were washed by moving them through the solution using the magnetic separation stand (Promega, catalog No. Z5332). The PBS was removed and the wash step was repeated one additional time. 400 µL 1×PBS was added for storage and the beads were stored at 4° C. Throughout the described procedure care was taken to avoid directly touching the beads with a pipette tip, applying forceful pipette mixing or excessive vortexing.

Example 2

Preparing Antibody Conjugated Magnetic Agarose Beads

About 20 of Protein A+G conjugated beads prepared as described in the previous Example were transferred to a clean 0.65 mL microcentrifuge tube. The storage solution was removed and 300 µL of 1×PBS was added to the beads. The beads were washed by moving them through the PBS solution using the magnetic separation stand. The PBS solution was removed and 5 µg of Phospho-S6 Ribosomal Protein (Ser235/236) (D57.2.2E) XP® rabbit monoclonal antibody, catalog No. 4858 (Cell Signaling Technology, Danvers Mass.) was added to the beads. It was experimentally determined that optimal results were achieved when the antibody was provided in a medium that did not contain bovine serum albumin (BSA) or glycerol. The antibody-bead mixture was incubated on the tube rotator at low speed, 4° C. for 3 hours at minimum, usually overnight. The tube was removed from the rotator and centrifuged briefly for less than 2 seconds. The unbound antibody was removed from the beads and 300 µL of 1×PBS was added. The beads were washed by moving them through the solution using the magnetic separation stand. The PBS solution was removed and the wash step was repeated one additional time. 400 µL of 1×PBS was added for storage and the beads were stored at 4° C.

Example 3

Cross-Linking an Antibody to Protein A+G Magnetic Agarose Beads

The antibody-conjugated Protein A+G beads prepared as described in the previous Example were transferred to a clean microcentrifuge tube by manual pipetting using a wide orifice pipette tip. The microcentrifuge tube was placed on a magnetic stand and the PBS solution transferred with the beads was removed. 300 µL of freshly prepared 0.2M solution of triethanolamine (Sigma-Aldrich, catalog No. 90279) at pH 8.2 was added to the beads, the bead suspension was briefly vortexed then centrifuged and the supernatant removed. The wash with triethanolamine was repeated once more. 300 µL of freshly prepared 25 mM solution of dimethyl pimelimidate dihydrochloride (DMP, Sigma-Aldrich, catalog No. D8388) in 0.2M triethanolamine at pH 8.2 was added to the beads. The bead suspension was briefly vortexed, then centrifuged. The microcentrifuge tube containing the bead suspension was placed on a lab rotator and the beads were incubated while rotating for 45 minutes at room temperature. The beads were subsequently centrifuged and the supernatant removed. 300 µL of freshly prepared 0.1M solution of ethanolamine (Sigma-Aldrich, catalog No. 398136) at pH 8.2 was added. The bead suspension was vortexed then centrifuged and the supernatant removed. The ethanolamine wash step was repeated once more. The microcentrifuge tube containing the bead suspension was placed on a lab rotator and the beads were incubated in the ethanolamine solution for 1 hour at room temperature while rotating. The supernatant was subsequently removed, the beads were washed twice with 300 µL of 1×PBS buffer (Fisher Scientific, catalog No. BP24384300) and stored in 1×PBS buffer at 4° C.

Example 4

Assembling a Multiplexed Target-Encoded Bead Array

Monoclonal antibodies specific for protein targets involved in the mechanistic target of rapamycin (mTOR) and other pathways were purchased from Cell Signaling Technology (Danvers, Mass.), R&D Systems (Minneapolis, Minn.) and ThermoFisher (Waltham, Mass.). The antibodies purchased from Cell Signaling Technology included Phospho-p70 S6 Kinase (Thr389) (108D2) rabbit mAb (catalog No. 9234), Phospho-p70 S6 Kinase (Thr389) (1A5) mouse mAb (catalog No. 9206), p70 S6 Kinase (49D7) rabbit mAb (catalog No. 2708), Phospho-S6 Ribosomal Protein (Ser235/236) (D57.2.2E) XP® rabbit mAb (catalog No. 4858), Phospho-S6 Ribosomal Protein (Ser240/244) (D68F8) XP® rabbit mAb (catalog No. 5364), S6 Ribosomal Protein (54D2) mouse mAb (catalog No. 2317), 4E-BP1 (53H11) rabbit mAb (catalog No. 9644), Phospho-4E-BP1 (Thr37/46) (236B4) rabbit mAb (catalog No. 2855), Phospho-4E-BP1 (Ser65) (D9G1Q) rabbit mAb (catalog No. 13443), Phospho-4E-BP1 (Thr70) (D7F61) rabbit mAb (catalog No. 13396), Phospho-Akt (Pan) (Ser473) (D9E) XP® rabbit mAb (catalog No. 4060), Phospho-Akt1 (Ser473) (D7F10) XP® rabbit mAb (catalog No. 9018), Phospho-Akt (Pan) (Thr308) (D25E6) XP® rabbit mAb (catalog No. 13038), Akt (pan) (C67E7) rabbit mAb (catalog No. 4691), Akt1 (C73H10) rabbit mAb (catalog No. 2938), Phospho-TSC2 (Thr1462) (5B12) rabbit mAb (catalog No. 3617), TSC2 (D93F12) XP® rabbit mAb (catalog No. 4308), Phospho-Gsk3b (Ser9) (D85E12) XP® rabbit mAb (catalog No. 5558) and GSK3b (D5C5Z) XP® rabbit mAb (catalog No. 12456). The antibodies purchased from R&D Systems included Human Phospho-Histone H2AX (Ser139) (catalog No. AF2288), Human/Mouse/Rat Phospho-ATM (Ser1981) (catalog No. AF1655), Human Phospho-BRCA1 (Ser1423) (catalog No. AF1386), Human Phospho-Chk2 (Thr68) (catalog No. AF1626), Human Phospho-Chk1 (Ser345) (catalog No. AF2475). The total number of unique capture reagents, i.e. antibodies included in the bead array, was greater than 50.

Figure 3:
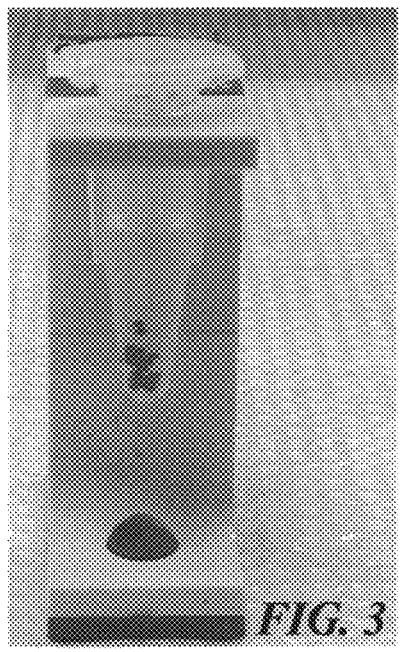
FIG. 3 is a photograph of a suspension bead array containing multiple distinct reactive sites inside a microcentrifuge tube placed on a magnetic bead separation rack.

Individual antibodies were conjugated to magnetic agarose beads using procedures described in the previous Examples. A series of multiplexed bead arrays for profiling multiple targets in the mTOR pathway were assembled by selecting between 1 and 3 beads conjugated to one of the antibodies listed above and subsequently combining beads, which were conjugated to different antibodies, in a single 1.7 mL microcentrifuge tube. For example, FIG. 3 shows a multiplexed suspension bead array for measuring total protein abundance and site-specific phosphorylation of two proteins: 4E-BP1 and p70 S6 Kinase. The bead array shown in FIG. 3 contained Cell Signaling Technology antibodies #2855, #9644, #2708 and #9234 individually conjugated to 700-790 µm diameter magnetic agarose beads. The individual reactive sites of this four-plex bead array did not possess distinguishable optical properties or mass tags nor did they have positional encoding. However, target analytes captured by the bead array were readily identifiable by mass spectrometry because information about an identity and a molecular weight of the target analytes was provided in the microarray decoding table. The data in the decoding table was generated by independently validating each of the antibodies included in the bead array. An antibody validation process included the steps of (1) performing immunoaffinity enrichment of peptide analyte(s) from a digested cell lysate using a single bead conjugated to a specific antibody, (2) using mass spectrometry to measure the analyte(s) captured by the bead-conjugated antibody and (3) assigning the detected analyte signal(s), i.e. peak(s) in the mass spectra to specific peptide sequence(s). The peak assignment was performed using available information about the precursor protein sequence, the antibody specificity, e.g. the probable epitope and the digestive enzyme specificity. Specifically, in this Example all precursor proteins were of human origin and the digestive enzyme was mass spectrometry sequencing grade trypsin. It was determined experimentally that peptide targets captured by individual reactive sites of this bead array had sufficiently unique molecular weights to enable unambiguous identification of a particular target based on a single value, which was derived from the molecular weight of the target. Specifically, the reactive site containing antibody #9644 for measuring total protein abundance of 4E-BP1 captured proteolytic fragment RAGGEESQFEMDI (SEQ ID NO: 1) derived from the C-terminus of 4E-BP1, which contained one missed cleavage site and had an average calculated [MH]+ m/z of 1469.58. The same reactive site also captured proteolytic fragment AGGEESQFEMDI (SEQ ID NO: 2), which contained no missed cleavage sites and had an average calculated [MH]+ m/z of 1313.39. The reactive site containing antibody #2855 for measuring phosphorylation of 4E-BP1 at Thr37 and Thr46 captured proteolytic fragment VVLGDGVQLPPGDYSTTPGGTLFSTTPGGTR (SEQ ID NO: 3), which contained two phospho-groups and had an average calculated [MH]+ m/z of 3209.32. The reactive site containing antibody #2855 also captured proteolytic fragment with the same sequence but a single phospho-group, which had an average calculated [MH]+ m/z of 3129.35.

Example 5

Cell Lysis, Protein Digestion and Peptide Extraction

MKN45 human gastric cancer cells were cultured using the RPMI 1640 medium supplemented with 20% FBS. Cells grown on a plate to about 80% confluence were washed twice with cold PBS, 1 mL of urea lysis buffer was added to the plate, the cells were scraped from the plate and collected in a 50 mL FALCON™ centrifuge tube. The cell suspension was sonicated using a microtip in 3 to 5 bursts for 20 seconds each time at 15 W output. The cell suspension was cooled on ice for 1 min between the bursts. The lysate was cleared by centrifugation at 5,000 g for 15 min at room temperature and the supernatant transferred to a clean tube for enzymatic digestion.

The cleared cell supernatant was subjected to reduction, alkylation and enzymatic digestion. $\frac{1}{278}$ volume of 1.25M DTT was mixed with the supernatant and incubated at 40° C. for 30 min. The solution was briefly cooled on ice until it reached room temperature. $\frac{1}{10}$ volume of freshly prepared 100 mM iodoacetamide solution was subsequently added and incubated for 15 min at room temperature in the dark. The solution was diluted 5-fold with 0.2M ammonium bicarbonate digestion buffer. $\frac{1}{100}$ volume of 1 mg/mL sequencing-grade trypsin stock was added and the digestion reaction allowed to proceed overnight at 37° C. with mixing. For digestion with chymotrypsin, $\frac{1}{60}$ volume of 1 mg/mL chymotrypsin stock was added instead of trypsin and the digestion reaction allowed to proceed overnight at 37° C. with mixing.

Immediately after the digestion reaction the digested cell lysate was purified on 0.7 mL SEP-PAK® C18 columns from Waters Corporation, catalog No. WAT051910. Prior to loading peptides from the protein digest on the column, the digested lysate was acidified by adding $\frac{1}{20}$ volume of 10% TFA to the final concentration of 0.5% TFA. The solution was allowed to stand for 15 min on ice, which resulted in formation of a precipitate. The acidified peptide solution was centrifuged for 15 min at 1,780 g at room temperature and the peptide-containing supernatant was transferred into a clean 50 mL conical tube without dislodging the precipitated material.

A reservoir made from a 10 cc syringe, which had the plunger removed, was connected to the short end of the SEP-PAK® column. 5 mL of 100% MeCN was applied to pre-wet the column. The column was washed sequentially with 1 mL, 3 mL, and 6 mL of 0.1% TFA solution. The acidified and cleared digest was loaded on the column and washed sequentially with 1 mL, 3 mL, and 6 mL of 0.1% TFA solution followed by wash with 2 mL of 5% MeCN, 0.1% TFA solution. The peptides were eluted by 3 sequential washes, each with 2 mL of 0.1% TFA, 50% acetonitrile solution. Solution containing the eluted peptide was placed inside a −80° C. freezer for at least 2 hr to overnight. The frozen peptide solution was lyophilized using a standard lyophilizer for a minimum of 2 days to assure TFA has been removed from the sample. The lyophilized digested peptides can be kept inside a sealed microcentrifuge tube at −80° C. for several months.

Example 6

Performing Multiplexed Immunoaffinity Enrichment of Peptides from an Enzymatically Digested Cell Lysate Using Antibody-Conjugated Magnetic Beads A lyophilized cell lysate prepared as described in the previous Example was suspended in the binding buffer (2.5M NaCl in 25 mM Tris, 192 mM glycine, pH ~8.3) to the final concentration of about 2 mg/mL. The lysate suspension was homogenized by repeated manual pipetting while avoiding forming bubbles in the solution. The cell lysate solution was centrifuged at 14,000 RPM at 4° C. for 5 min. The clear supernatant was transferred to a new 1.7 mL microcentrifuge tube. Using a wide orifice pipette tip, a suspension bead array containing 20 antibody-conjugated magnetic beads prepared as described in Example 4 was transferred to a clean 0.65 mL microcentrifuge tube. The clear cell lysate supernatant was added to the beads while avoiding forming bubbles in the lysate. This was followed by a brief, e.g. less than 1 second centrifugation of the tube to collect droplets from the tube walls. The suspension of beads mixed with the cell lysate supernatant was incubated on a rotator at low speed at 4° C. for at least 3 hours, in some cases overnight or longer than 24 hours. The tube was briefly centrifuged, the beads removed using the magnetic QuicPick device and transferred to a clean 0.65 mL tube containing 300 µL of 2.5M NaCl solution in deionized water. An additional 340 µL of the 2.5M NaCl solution was added to the tube. The beads were incubated on the rotator at low speed at room temperature for 10 minutes. The tube was briefly centrifuged and about 300 µL of the solution removed by pipetting. Using the magnetic QuicPick device the beads were transferred to a clean 0.65 mL tube containing 300 µL of deionized water. The beads were washed by repeatedly moving the tube on the magnetic separation stand and further incubated for about 2 minutes at room temperature. Using pipetting with a wide orifice pipette tip, the beads were transferred into a clean 0.65 mL tube containing about 200 µL of deionized water and stored at 4° C.

Example 7

Assembling a Microwell Slide

A microwell slide was prepared by affixing a silicone gasket to the conductive side of an ITO-coated glass microscope slide. Specifically, a surface of the silicone gasket was first cleaned from any residual dust particles by using a strip of adhesive tape. The gasket was then placed on top of one or two sheets of a low lint tissue, such as KIMWIPES® positioned on a flat surface of a laboratory bench. Dry ITO-coated surface of the glass slide was placed in contact with the silicone gasket and the slide was manually pressed into the gasket to form a watertight seal. The seal quality was visually checked and any residual air pockets were removed by pressing locally on the slide. Overall dimensions of the fabricated microwell slide were 25 mm×75 mm×1.4 mm.

Example 8

Forming a Bead Array on the Microwell Slide

The microwell slide was prepared as described in the previous Example and attached to the PROPLATE® 8-well slide module containing 8 rectangular chambers, each of the chambers having internal dimensions of 7 mm×16 mm. For certain applications the 1.6 mm thick clear silicone gasket included in the standard PROPLATE® slide module was replaced with a thinner 1.3 mm clear silicone gasket in order to better accommodate the 1.4 mm thick microwell slide. The microwell slide was secured to the PROPLATE® module by PROPLATE® stainless steel spring clips.

Figure 4:
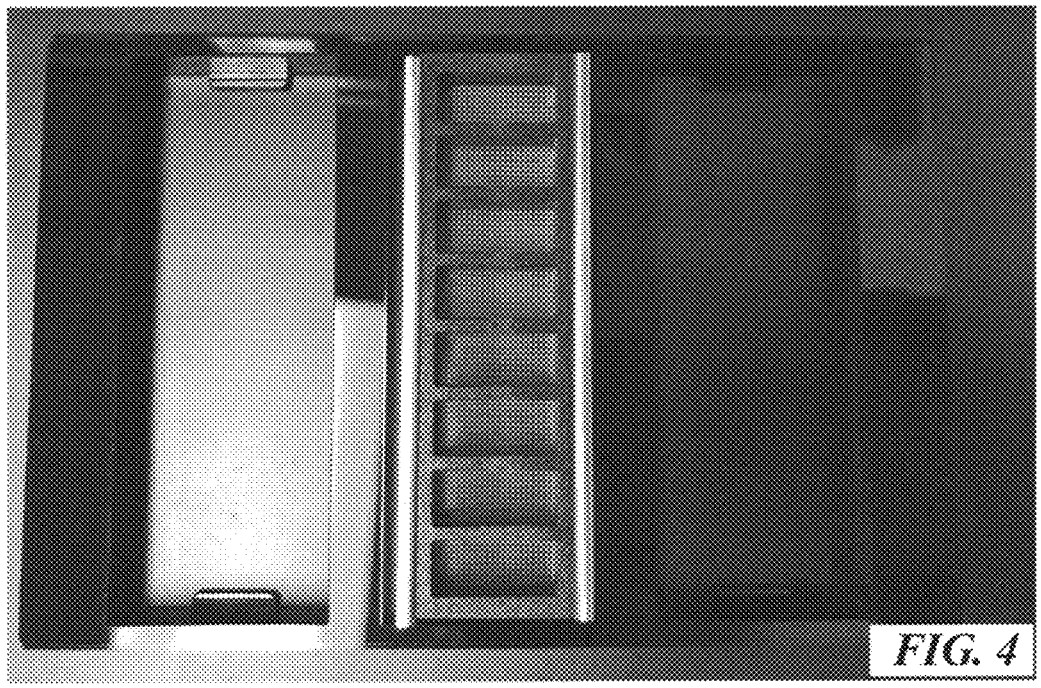
FIG. 4 is a photograph of a microwell slide attached to the 8-well PROPLATE® module and positioned in a middle section of the PROPLATE® tray for spring modules.

The assembly containing the microwell slide attached to the PROPLATE® module was subsequently placed in the middle section of a three-section PROPLATE® tray for spring clip modules, as depicted in FIG. 4. About 300 µL of deionized water was dispensed into each of the 8 chambers and the PROPLATE® tray was centrifuged at 2700 RPM for 5 minutes at room temperature to facilitate entry of water into the 0.5 mm diameter wells of the microwell slide.

An aqueous suspension containing 42 magnetic agarose beads in the 0.375-0.420 mm diameter range was pulled into a wide orifice pipette tip by pipetting and then randomly dispensed into 2 of the 8 chambers of the PROPLATE® module. The PROPLATE® tray was placed on a standard laboratory microtiter plate shaker and subjected to mechanical agitation for 1 to 2 minutes to help distribute the beads into microwells. The PROPLATE® tray was subsequently centrifuged at 2700 RPM for 1 minute at room temperature to help bring the beads down to the bottom of their respective microwells. All beads were therefore positioned about 80 to 120 microns below the surface of the microwell slide.

Figure 5:
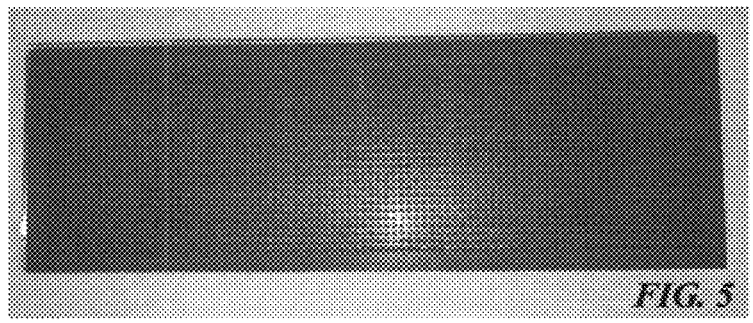
FIG. 5 is a photograph of a bead array, in which 400 µm magnetic agarose beads are arrayed inside 500 µm wells on a microwell slide.

The microwell slide attached to the PROPLATE® module was removed from the PROPLATE® tray and a 3"×1"×⅛" thick nickel plated magnetized through thickness neodymium magnet (K&J Magnetics, catalog No. BZ0X02) was placed underneath the module between the stainless steel clips to help retain the beads in their locations. Bulk water was withdrawn from each chamber by pipetting, with the pipette tip pointing toward a sidewall of the chamber so as not to disturb the bead array, the magnet and the stainless steel clips removed and the microwell slide detached from the PROPLATE® module. The microwell slide was placed on top of the magnet and residual drops of water remaining on the surface were removed by gently pressing a sheet of a low lint absorbent tissue, such as KIMWIPES® or alternatively a paper towel against the slide surface. None of the beads, which remained positioned about 80 to 120 microns below the slide surface, were displaced by this procedure, as seen in FIG. 5. It was observed that while bulk water was completely removed from the surface of the microwell slide, individual 0.5 mm diameter microwells retained sufficient amount of liquid, which remained inside the microwells for about 5 to 10 minutes under standard conditions, e.g. relative humidity between 10% and 90%, temperature between 18° C. and 32° C. As long as some amount of liquid remained in the microwells, the agarose beads retained their fully hydrated size. Only after the residual liquid had evaporated from the microwells did the beads shrink to a fraction of their original size as a result of desiccation.

Example 9

Eluting Analytes from a Bead Array

A bead array containing 13 beads was fabricated on a microwell slide using the procedure described in the previous Example. All individual beads within the bead array were conjugated to the previously described Phospho-S6 Ribosomal Protein (Ser235/236) monoclonal antibody #4858 and contained captured proteolytic fragments of S6 Ribosomal Protein dually phosphorylated at Ser235 and Ser236.

Droplets of water present on the surface of the microwell slide after separation from the PROPLATE® module were removed by gently touching the slide surface with an absorbent tissue. The microwell slide was immediately placed at the center of the matrix deposition area of iMatrixSpray and 10 cycles of matrix deposition were applied to the bead array. Note that the first matrix deposition cycle should commence no later than 5 minutes, preferably within 3 minutes after removing droplets of water from the slide surface in order to achieve optimal mixing of the MALDI matrix solution with the residual liquid remaining inside the microwells. The matrix deposition parameters of iMatrixSpray were set as follows: Height: 60 mm; Line Distance: 0.5 mm; Speed: 60 mm/s; Density: 5 µL/cm$^2$; Number of cycles: 10; Delay: 0 sec; Spray area width: 80 mm; Spray area depth: 30 mm. The matrix solution contained α-Cyano-4-hydroxycinnamic acid (CHCA) at 5 mg/mL, 50% acetonitrile (v/v), 0.4% trifluoroacetic acid and 4 mM diammonium citrate.

Once the final matrix deposition cycle was completed, the bead array was allowed to air-dry, which required about 25 to 30 minutes. The microwell slide was visually examined to verify that no microwells contained residual liquids and that all beads had been reduced in size due to desiccation. The silicone gasket was separated from the microscope slide. Some of the dried agarose beads stuck to the silicone and were removed from the slide along with the gasket. The remaining beads were removed using a stream of compressed air from an air duster, which was directed at the slide surface. It was observed that while dried agarose beads were readily displaced from their positions by the compressed gas, the crystals of MALDI matrix remained firmly attached to the slide surface and localized within their respective microspots.

Figure 6A:
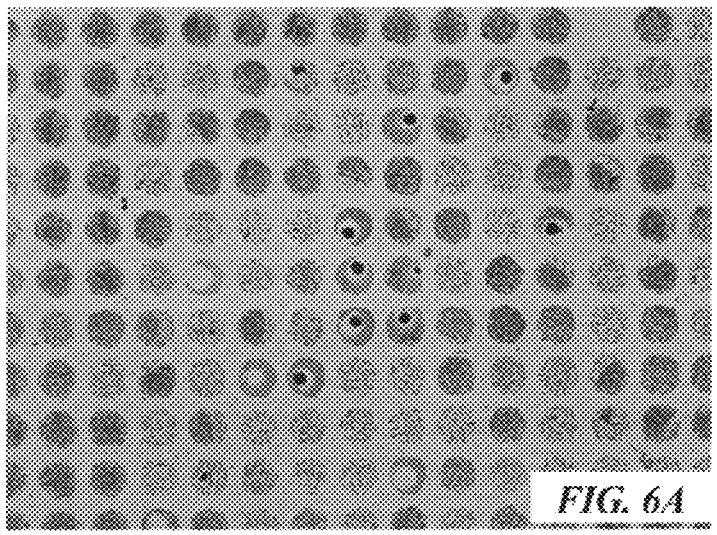
FIG. 6A is a bright field microscope image of an array of 500 µm diameter microspots containing crystals of CHCA MALDI matrix, with some microspots also containing agarose beads that were reduced in size due to desiccation.
Figure 6B:
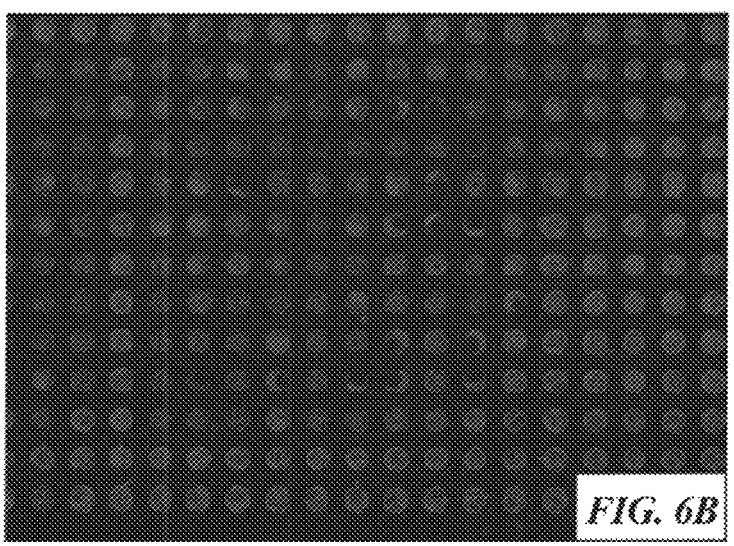
FIG. 6B is a bright field microscope image of an array of 500 µm diameter microspots containing crystals of CHCA MALDI matrix after removal of the agarose beads.

FIG. 6A is a bright field microscope image of an array of spots containing CHCA MALDI matrix, which was recorded prior to removal of the beads from the slide by compressed air. Agarose beads, which had been reduced in size due to desiccation, are visible in 9 spots. In additional 4 spots the beads were not present but the spot shape, e.g. non-uniform distribution of CHCA matrix indicated prior presence of a bead, which had likely been removed from the slide along with the silicone gasket. The remaining spots contained no beads and displayed more uniform distribution of the matrix across the spot. FIG. 6B is a bright field microscope image of an unrelated array of spots containing CHCA MALDI matrix, in which all beads had been removed from the slide using compressed air. Note that spots formed in locations that initially contained a bead exhibited characteristic "crescent" or "donut" shapes with areas containing little or no CHCA matrix. In contrast, spots formed in locations initially devoid of a bead generally exhibited more uniform matrix coverage. The images shown in FIG. 6A and FIG. 6B were acquired on CYTATION™ 3 multi-mode reader from BioTek (Winooski, Vt.).

Example 10

Acquiring Mass Spectrometric Data from an Array of Microspots

An array of microspots on the ITO-coated surface of a microscope slide was prepared using procedures described in the previous Example. The slide was placed into the MTP Slide Adapter II for MALDI Imaging. A custom geometry file provided by Bruker Daltonics (Billerica, Mass.) enabled consecutive acquisition of mass spectrometric data from a square grid array of 2288 spots, each spot having a variable diameter of up to 600 In some cases, the data was acquired from smaller sections within the array, which contained between 50 and 500 spots.

The MALDI TOF MS data was acquired on Bruker Autoflex Speed MALDI TOF-TOF mass spectrometer from Bruker Daltonics using flexControl software provided with the instrument. The data was acquired in the linear positive mode, in 1,000 to 7,000 m/z mass range, using the laser repetition rate of 2 kHz. A total of 20,000 single-shot spectra were typically collected from a single microarray spot and co-added, although in some cases high quality spectra were obtained from as few as 100 shots. In some cases, more than 100,000 single-shot spectra were collected from a single microarray spot without completely depleting analytes present in the spot. The spectra were acquired from multiple locations within each spot using either the random walk or the inverse spiral method, both methods provided in the flexControl software.

Example 11

Analyzing Mass Spectrometric Data

MS datasets were analyzed using flexAnalysis and BIOTOOLS™ software from Bruker Daltonics. In some cases, files containing MS data were converted into .txt format and analyzed using the public domain software mMass. Mass spectra were analyzed to determine key parameters such as mass accuracy, spectral resolution, as well as signal-to-noise ratio, relative intensity and peak area of individual peaks present in a particular mass spectrum.

Example 12

Microarray Reactive Site Configured for Capturing Multiple Target Analytes

In this Example the capture agent is a monoclonal antibody Phospho-Met (Tyr1234/1235) (D26) XP® Rabbit mAb, catalog No. 3077 that was acquired from Cell Signaling Technology (Danvers, Mass.). Met, also known as hepatocyte growth factor receptor (HGFR) is a tyrosine kinase with a MW of 145 kDa. The entry number and the entry name for this protein in the UniProt (Universal Protein Resource) database are P08581 and MET_HUMAN, respectively. According to the product description provided on the manufacturer's website, which was accessed on Feb. 20, 2017, #3077 antibody " . . . detects endogenous levels of Met only when phosphorylated at Tyr1234/1235". The #3077 antibody is validated for applications that include western blotting, immunoprecipitation, immunohistochemistry (par-affin), immunohistochemistry (frozen), immunofluorescence (immunocytochemistry) and flow cytometry. Using the procedures described in the previous Examples, the #3077 antibody was conjugated to Protein A+G agarose beads and incubated with 1 mg of tryptic digest of lysed MKN-45 cells. A mass spectrum was recorded in the linear positive mode after performing immunoaffinity purification (IAP) reaction and eluting the bound analytes from a single bead. MS measurements were also performed in the reflector positive mode (data not shown). Three strong peaks were detected in the mass spectrum at m/z values of 1853.06, 2210.27 and 2647.54. The assignment of these peaks to specific peptide analytes was made based on the following data: the known amino acid sequence of the precursor protein, i.e. Met kinase, the known specificity of the digestive enzyme, i.e. trypsin and the probable epitope. With respect to the latter, although the precise epitope sequence is not disclosed, the manufacturer's website states that the "monoclonal antibody is produced by immunizing animals with a synthetic phosphopeptide corresponding to residues surrounding Tyr1234/1235 of human Met". Based on the above information, the peak assignments were made as follows: the 1853.06 peak was assigned to a peptide DMYDKE[pY][pY]SVHNK (SEQ ID NO: 4), which has a calculated MH+ value of 1852.82, the 2210.27 peak was assigned to a peptide DMYDKE[pY][pY]SVHNKTGAK (SEQ ID NO: 5), which has a calculated MH+ value of 2210.23, and the 2647.54 peak was assigned to a peptide DMYDKE[pY][pY]SVHNKTGAKLPVK (SEQ ID NO: 6), which has a calculated MH+ value of 2647.81. In the amino acid sequences listed above [pY] denotes phosphorylated tyrosine. It is noted that the peak assignments did not require the peptide fragmentation by mass spectrometry or the use of tandem mass spectrometry (MS-MS). In this Example, the multiple target analytes are proteolytic fragments of a precursor protein containing different numbers of missed cleavage sites.

Example 13

Microarray Reactive Site Configured for Capturing a Variable Number of Target Analytes In this Example the capture agent is Phospho-S6 Ribosomal Protein (Ser235/236) (D57.2.2E) XP® Rabbit monoclonal antibody, catalog No. 4858 that was purchased from Cell Signaling Technology. According to the description provided on the manufacturer's website, which was accessed on Feb. 20, 2017, #4858 antibody " . . . detects endogenous levels of ribosomal protein S6 only when phosphorylated at Ser235 and 236". The entry number and the entry name for human S6 ribosomal protein in the UniProt database are P62753 and RS6_HUMAN, respectively. Conjugation of the antibody to magnetic agarose beads and immunoaffinity enrichment reactions were performed using procedures described in the previous Examples. The immunoaffinity enrichment was performed independently from two samples, which were prepared from trypsin-digested lysates of MKN-45 cells cultured in the absence and presence of hydrogen peroxide. The exposure of mammalian cells to hydrogen peroxide is known to cause elevated levels of protein phosphorylation.

Mass spectra of proteolytic peptides captured from the digested lysates of MKN-45 cells grown in the absence of hydrogen peroxide exhibited a total of 4 distinct peaks spaced apart by about 80 m/z units. Mass spectra of proteolytic peptides captured from the digested lysates of MKN- 45 cells grown in the presence of hydrogen peroxide exhibited a total of 6 distinct peaks. Four of the peaks were present at identical m/z positions in the two spectra while the two additional peaks unique to the hydrogen peroxide-treated cells appeared at higher m/z and were also spaced apart by about 80 m/z. Using available information about the protein sequence, the antibody specificity and the digestive enzyme specificity, all detected peaks were assigned to a proteolytic peptide RLSSLRASTSKSESSQK (SEQ ID NO: 7) consisting of amino acids 233 through 249 of human S6 ribosomal protein and containing 3 missed cleavage sites and a variable number of phosphorylated sites. Predicted average m/z values for the differentially phosphorylated peptides were: 2013.1 (2 phospho sites), 2093.0 (3 phospho sites), 2173.0 (4 phospho sites), 2252.9 (5 phospho sites), 2332.9 (6 phospho sites) and 2412.9 (7 phospho sites). Note that peptides containing no phosphorylated sites or a single phosphorylated site were not detected because of the specificity of the antibody, which recognizes the peptide sequence the only when both Ser235 and Ser236 are phosphorylated. Furthermore, the presence of multiple missed cleavage sites in the detected peptide was consistent with the specificity of this digestive enzyme because it is known that trypsin may not cleave after Lys or Arg residues proximal to a phosphorylated residue. In this Example, the microarray reactive site is capable of binding at least 6 distinct peptide analytes, which differ in the quantity of post-translationally modified sites.

Example 14

Microarray Reactive Site Configured for Capturing Proteolytic Peptides of Human and Mouse Origins In this Example the capture agent is Goat Anti-Aconitase 2 (aa541-555) polyclonal antibody, catalog No. EB09858 supplied by Everest Biotech (Upper Heyford, Oxfordshire UK). The capture agent recognizes an internal sequence of protein ACO2, also known as mitochondrial aconitate hydratase. The entry number and the entry name for human ACO2 in the UniProt database are Q99798 and ACON_HUMAN, respectively. The entry number and the entry name for mouse ACO2 in the UniProt database are Q99KI0 and ACON_MOUSE, respectively. The sequence of an immunizing peptide used for the antibody production is QDTYQHPPKDSSGQH (SEQ ID NO: 8). Conjugation of the antibody to magnetic agarose beads and immunoaffinity enrichment reactions were performed using procedures described in the previous Examples. The immunoaffinity enrichment was performed independently from two samples, namely trypsin-digested lysates of cultured MKN-45 cells and trypsin-digested lysates of a mouse brain tissue. The digestive enzyme used for sample preparation was bovine trypsin from Worthington Biochemical Corp (Lakewood, N.J.), catalog No. LS02119.

Mass spectra of proteolytic peptides captured from the digested MKN-45 lysates exhibited a pair of prominent peaks between 4,400 and 4,800 m/z and another pair of peaks between 2,200 and 2,400 m/z. Using available information about the protein sequence, the antibody specificity and the digestive enzyme specificity, the pair of peaks observed in the higher m/z range was assigned to proteolytic peptides LEAPDADELPKGEFDPGQDTYQHPPKDSSGQHVDVSPTSQR (SEQ ID NO: 9) and FRLEAPDADELPKGEFDPGQDTYQHPPKDSSGQHVDVSPTSQR (SEQ ID NO: 10), which have predicted average m/z values of 4477.7 and 4781.1, respectively. The pair of peaks observed in the lower m/z range was assigned to the double-charged forms of the same peptides.

Mass spectra of proteolytic peptides captured from the digested mouse brain tissue exhibited a pair of prominent peaks between 3,800 and 4,000 m/z and a series of smaller peaks below 2,500 m/z. Using available information about the protein sequence, the antibody specificity and the digestive enzyme specificity, the pair of peaks observed between 3,800 and 4,000 m/z was assigned to proteolytic peptides FKLEAPDADELPRSDFDPGQDTYQHPPKDSSGQR (SEQ ID NO: 11) and KFKLEAPDADELPRSDFDPGQDTYQHPPKDSSGQR (SEQ ID NO: 12), which have predicted average m/z values of 3846.1 and 3974.3, respectively. Two of the peaks observed in the lower m/z range were assigned to the double-charged forms of the same peptides.

In this Example, the antibody recognizes and specifically binds proteolytic peptides derived from both human and mouse forms of ACO2 because the epitope sequence is preserved in these proteins. The differences in detected m/z values between the proteolytic peptides of human and mouse origins are ascribed to a combination of two factors: (1) different recognition sites for the digestive enzyme, e.g. trypsin in the corresponding precursor proteins, which result in different length of the proteolytic peptides and (2) amino acid substitutions in the corresponding precursor proteins, which do not alter recognition sites for the digestive enzyme but nevertheless cause a mass difference.

This Example demonstrates a method of detection and quantification of proteins derived from two different species, namely human (*Homo sapiens*) and mouse (*Mus musculus*). One application of this technology is a single-plex or multiplex analysis of protein expression and/or protein modification in cell, tissue and organ transplants, e.g. tumor xenografts.

Example 15

Microarray Reactive Site Configured for Capturing Proteolytic Peptides Produced by Different Digestive Enzymes In this Example the capture agent is Phospho-4E-BP1 (Thr37/46) (236B4) Rabbit monoclonal antibody, catalog No. 2855 purchased from Cell Signaling Technology. According to the description provided on the manufacturer's website, which was accessed on Feb. 20, 2017, #2855 antibody " . . . detects endogenous levels of 4E-BP1 only when phosphorylated at Thr37 and/or Thr46. This antibody may cross-react with 4E-BP2 and 4E-BP3 when phosphorylated at equivalent sites". The entry number and the entry name for human Eukaryotic translation initiation factor 4E-binding protein 1 in the UniProt database are Q13541 and 4EBP1_HUMAN, respectively. Conjugation of the antibody to magnetic agarose beads and immunoaffinity enrichment reactions were performed using procedures described in the previous Examples. The immunoaffinity enrichment of proteolytic peptides containing the antibody recognition site was performed from several samples, which were prepared by enzymatic digestion of MKN-45 cell lysates using the following digestive enzymes: sequencing grade modified trypsin (Promega catalog No. V5117), sequencing grade chymotrypsin (Promega catalog No. V1061), pepsin (Promega catalog No. V1959), MS grade Lys-C protease (ThermoFisher catalog No. 90051), MS grade Lys-N protease (ThermoFisher catalog No. 90300), MS grade Glu-C protease (ThermoFisher catalog No. 90054), sequencing grade Arg-C protease (Promega catalog No. V1881), thermolysin (Promega catalog No. V4001), elastase (Promega catalog No. V1891).

Mass spectrometric analysis of proteolytic peptides eluted from the beads after the immunoaffinity enrichment was performed in the linear positive mode as described in the previous Examples. Positions of peaks observed in the mass spectra were in agreement with the m/z values predicted for the epitope-containing fragments of 4E-BP1 after digestion with a specific enzyme. For example, two strong peaks in the mass spectrum of trypsin-digested 4E-BP1 were observed near m/z 3129.4 and 3209.3 corresponding to the calculated average m/z values of single- and double-phosphorylated forms of the peptide VVLGDGVQLPPGDYSTTPGGTLF-STTPGGTR (SEQ ID NO: 3) containing amino acids 21 through 51 of human 4E-BP1, respectively. Likewise, the mass spectrum of pepsin-digested 4E-BP1 exhibited a strong peak near m/z of 1393.5 corresponding to a single-phosphorylated form of the peptide FSTTPGGTRIIY (SEQ ID NO: 13) containing amino acids 43 through 54 of human 4E-BP1. The mass spectrum of chymotrypsin-digested 4E-BP1 exhibited a pair of strong peaks near m/z of 1246.3 and 2053.3. The former peak was assigned to a single-phosphorylated form of the peptide STTPGGTRIIY (SEQ ID NO: 14) containing amino acids 44 through 54 of human 4E-BP1 and zero missed cleavages by chymotrypsin while the latter peak was assigned to a single-phosphorylated form of the peptide FSTTPGGTRIIYDRKFL (SEQ ID NO: 15) containing amino acids 43 through 59 of human 4E-BP1 and three missed cleavages by chymotrypsin.

The pepsin-digested samples also contain peptide ST[pT]PGGTL (SEQ ID NO: 16) (0 missed cleavages, MW 813.78), which is recognized by #2855 antibody. This peptide is derived from two proteins: 4E-BP1 and 4E-BP3 (UniProt entry number O60516). By contrast, the pepsin-digested peptide GGEESQFEMDI (SEQ ID NO: 17) (1 missed cleavage, MW 1242.31), which is recognized by the previously described #9644 antibody, is derived from 4E-BP1 but not 4E-BP3. Thus including both #2855 and #9644 antibodies creates a microarray, in which one capture agent recognizes an epitope that is found in two distinct proteins and the other capture agent recognizes an epitope that is found in only one of these proteins.

In a separate experiment, a reactive site containing the previously described antibody #4858 was added to the microarray. Both the #2855 and #4858 antibodies recognize epitopes, which lack proteolytic cleavage sites recognized by at least two of the following digestive enzymes: trypsin, chymotrypsin, pepsin, endoproteinase Glu-C and endoproteinase Asp-N.

Example 16

Non-Specific Binding of a Target Analyte to Distinct Reactive Sites of a Microarray Several identical microarrays featuring distinct reactive sites were produced using three phospho-specific antibodies #2855, #3077 and #4858 described in the previous Examples. Less than ten (three to five) replicate beads containing the same type of antibody were included in each microarray. Each microarray thus contained a total of nine reactive sites capable of binding proteolytic peptides derived from phospho-4E-BP1 (Thr37/46), phospho-Met (Tyr1234/1235) and phospho-S6 ribosomal protein (Ser235/236). The fabricated microarrays were incubated with a series of digested MKN-45 cell lysates prepared using the enzymes listed in the previous Example, namely trypsin, chymotrypsin, Glu-C protease, Lys-C protease and Lys-N protease. The immunoaffinity enrichment from each of the digested cell lysates was performed as described in Example 6 except that 2.5M NaCl was omitted from the binding buffer during the binding reaction and the beads were washed in 1×PBS buffer instead of the 2.5M solution of NaCl. Analytes captured by the individual reactive sites of each microarray were analyzed by mass spectrometry as previously described. The absence of 2.5M NaCl in the binding and wash buffers did not have a significant effect on the mass spectra of analytes captured from trypsin-digested cell lysates. In contrast, not using high salt in the binding and wash buffers during immunoaffinity enrichment performed from chymotrypsin-digested cell lysates had a significant effect on the mass spectra with a strong peak observed near m/z of 2222.5 in the spectra recorded from every reactive site irrespectively of the conjugated antibody. The non-specific 2222.5 peak was present in the mass spectra in addition to the analyte-specific peaks, which matched the expected m/z values of proteolytic fragments of the corresponding precursor proteins after chymotrypsin digestion. For example, mass spectra recorded from the phospho-4E-BP1 reactive sites exhibited the 2222.5 peak in addition to the 1246.3 and 2053.3 peaks identified in the previous Example. To identify the non-specifically binding compound responsible for the 2222.5 peak an eluate was collected from bovine serum albumin (BSA)-conjugated agarose beads, which have been exposed to a chymotrypsin-digested MKN-45 cell lysate. The eluate was analyzed by Edman degradation yielding a peptide sequence KAQKKDGKKRKRSRKESY (SEQ ID NO: 18), which has a predicted average [M+H]+ value of 2222.6 and tentative assignment to amino acids 21 through 38 of human Histone H2B type 1-C/E/F/G/I. The entry number and entry name for human Histone H2B type 1-C/E/F/G/I in the UniProt database are P62807 and H2B1C_HUMAN, respectively. The data was subsequently used to make an entry in the microarray decoding table, which contained information about the molecular weight of this non-specifically binding compound and the fact that this compound may appear in the mass spectra of samples of human origin such as human cell cultures that have been subjected to digestion with chymotrypsin.

Example 17

Specific Binding of a Target Analyte to Distinct Reactive Sites of a Microarray

Polyclonal antibodies used as capture agents were from Everest Biotech. These included: (1) goat anti-aconitase 2 antibody (catalog No. EB09857, immunogenic peptide sequence C-QHVDVSPTSQRLQ (SEQ ID NO: 19)); (2) goat anti-aconitase 2 (aa541-555) antibody (catalog No. EB09858, immunogenic peptide sequence C-QDTYQHPPKDSSGQH (SEQ ID NO: 20)); (3) goat anti-GPI/Neuroleukin antibody (catalog No. EB09739, immunogenic peptide sequence C-YREHRSELNLRR (SEQ ID NO: 21)) and (4) goat anti-IDH3B (aa369-383) antibody (catalog No. EB10997, immunogenic peptide sequence C-TTDFIKSVIGHLQTK (SEQ ID NO: 22))

Individual antibodies were conjugated to magnetic agarose beads using procedures described in the previous Examples. A 4-plex bead array containing 8 reactive sites was assembled by selecting 2 beads conjugated to one of the four antibodies listed above and combining beads conjugated to different antibodies in a single 1.7 mL microcentrifuge tube. The assembled microarray was subsequently reacted with 2 mg of chymotrypsin digested MKN-45 cell lysate prepared as described in the previous Examples. The reacted bead array was transferred on a microwell slide, analytes eluted from the beads and analyzed by MALDI TOF MS as described in the previous Examples.

Figure 7:
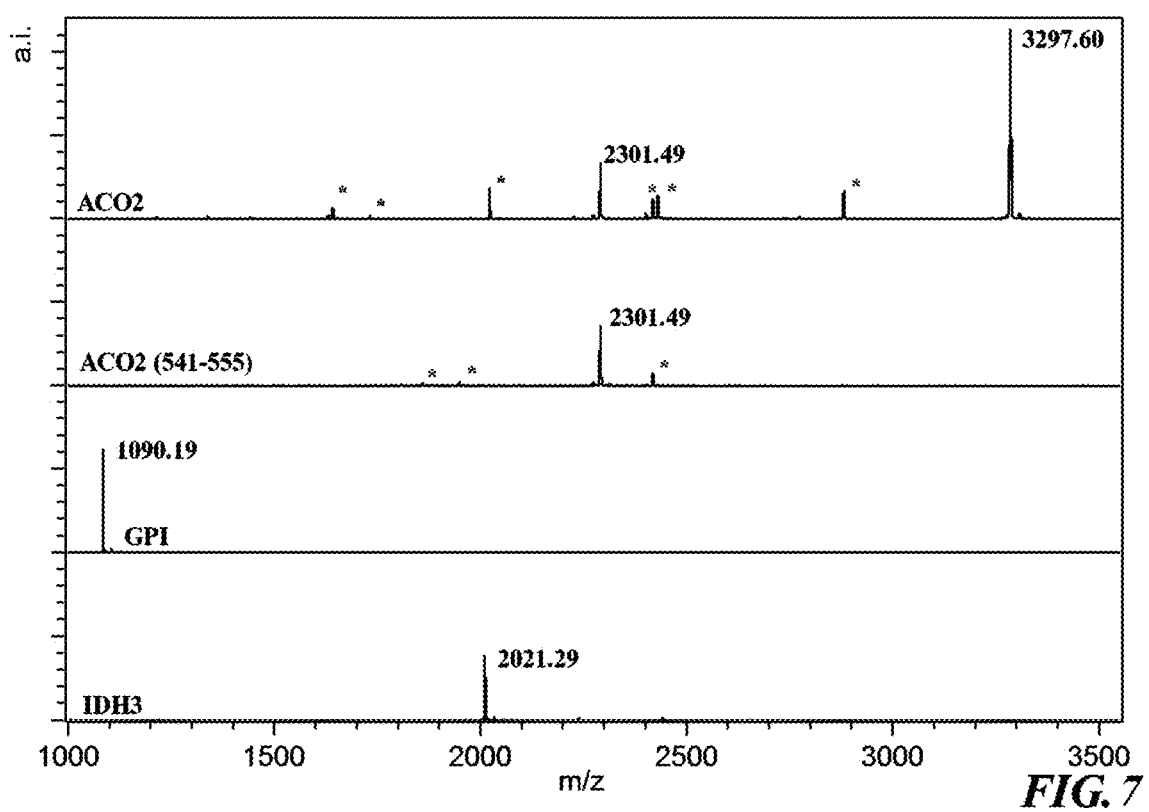
FIG. 7 shows exemplary mass spectra recorded from individual reactive sites of 4-plex bead array after exposing the array to enzymatically digested MKN-45 cell lysate.

A total of 8 mass spectra were identified that had one or several peaks with a signal-to-noise ratio greater than 3:1 in the 1,000-5,000 m/z mass range, matching the number of reactive sites present in the microarray. Four distinct pairs of mass spectra were identified corresponding to 4 distinct reactive sites of the microarray. Mass spectra recorded from the replicate reactive sites were very similar, e.g. had the same number of peaks with m/z values that varied by less than 0.1 between different spectra. FIG. 7 shows exemplary mass spectra acquired from individual reactive sites. Table 1 shows a decoding table for this microarray. In this Example the same peptide target with a sequence of QHPPKDSSGQHVDVSPTSQRL (SEQ ID NO: 23) and m/z of 2301.49 was captured by two distinct reactive sites of the microarray, namely reactive sites containing antibodies EB09857 and EB09858. These antibodies recognize adjacent sequences within human aconitase 2, which allows them to specifically bind the same proteolytic peptide. However, antibody EB09857 additionally captured a peptide with a sequence of QHVDVSPTSQRLQLLEPFDKWDGKDLED (SEQ ID NO: 24) and an m/z of 3297.60, which was not captured by antibody EB09858. Therefore, as shown in Table 1, the two reactive sites (ACO2 and ACO2 (541-555)) may be readily distinguished within the microarray, as both bind a target with m/z of 2301.49, yet only the former binds a target with m/z of 3297.60. In fact, the entry in the decoding table associated with the reactive site ACO2 (541-555) may optionally contain specific reference to the absence of a signal at m/z of 3297.60, as depicted by the *SIGNAL ABSENT* note in Table 1. Furthermore, in reference to FIG. 7 it can be seen that both the ACO2 and ACO2 (541-555) spectra also contain several additional lower intensity peaks. These peaks are specific to their respective antibodies and therefore information about their MW, m/z or TOF values may be included in the decoding table to further increase confidence in the target identification.

a signal, which is not detected at a specific m/z in a mass spectrum, as shown for the reactive site ACO2 (541-555) in Table 2.

In this Example, the ACO2 reactive site is associated with a combination that includes 2 distinct values: 2301.49 and 3297.60. The combination is both necessary and sufficient for identifying a target that specifically binds to the capture agent of that reactive site.

TABLE 2

Simplified microarray decoding table for a 4-plex microarray

| Reactive Site | Signal Detected in a Mass Spectrum (m/z) |
|---|---|
| ACO2 | 2301.49 AND 3297.60 |
| ACO2 (541-555) | 2301.49 AND NOT 3297.60 |
| GPI | 1090.19 |
| IDH3 | 2021.29 |

In some experiments, two goat anti-GAPDH (internal) antibodies from Everest Biotech were added to the microarray: catalog No. EB07069, immunogenic peptide sequence C-GVNHEKYDNSLK (SEQ ID NO: 27) and catalog No. EB06377, immunogenic peptide sequence C-HQVVSSDFNSDT (SEQ ID NO: 28). The epitope recognized by the latter antibody lacks a proteolytic cleavage site recognized by trypsin, while the epitope recognized by the former antibody contains such site, i.e. an internal lysine.

Example 18

Providing an Estimate of Relative Abundance of a Target Analyte in a Sample

A microarray was produced as described in the previous Examples using previously described antibodies #4858 and #9644, as well as phospho-p44/42 MAPK (Erk1/2) (Thr202/Tyr204) (D13.14.4E) XP® Rabbit monoclonal antibody, catalog No. 4370 from Cell Signaling Technology. According to the description provided on the manufacturer's website, which was accessed on Mar. 25, 2017, #4370 antibody "... detects endogenous levels of p44 and p42 MAP Kinase (Erk1 and Erk2) when dually phosphorylated at Thr202 and Tyr204 of Erk1 (Thr185 and Tyr187 of Erk2), and singly phosphorylated at Thr202".

TABLE 1

Microarray decoding table for a 4-plex microarray

| Reactive Site | Target ID | SEQ ID NO: | m/z |
|---|---|---|---|
| ACO2 | QHPPKDSSGQHVDVSPTSQRL | 23 | 2301.49 |
|  | QHVDVSPTSQRLQLLEPFDKWDGKDLED | 24 | 3297.60 |
| ACO2 (541-555) | QHPPKDSSGQHVDVSPTSQRL | 23 | 2301.49 |
|  | *SIGNAL ABSENT* |  | 3297.60 |
| GPI | YREHRSEL | 25 | 1090.19 |
| IDH3 | STTTDFIKSVIGHLQTKGS | 26 | 2021.29 |

A simplified version of a decoding table for the previously described microarray is shown in Table 2. In this Example, an amino acid sequence of a target captured by a reactive site is not provided and the reactive site is identified solely on the basis of one or more signals detected in a mass spectrum. Furthermore, a reactive site may be identified on the basis of It was experimentally determined that each of the 3 antibodies listed above was capable of specifically binding several targets from trypsin digested MKN-45 cell lysates. It was also experimentally determined that the relative intensity of signals from multiple targets captured by the same antibody did not vary considerably between different sample preparations, as long as cell culture and sample preparation conditions remained similar, e.g. same cell culture medium and same digestive enzyme were used. For example, the intensity ratio of peaks recorded from proteolytic fragments RAGGEESQFEMDI (SEQ ID NO: 1) and AGGEESQFEMDI (SEQ ID NO: 2) of 4E-BP1, which have m/z of 1469.6 and 1313.4, respectively, was consistently greater than 10:1. Peaks from the doubly- and triply-phosphorylated forms of the peptide RLSSLRASTSKSESSQK (SEQ ID NO: 7) were about 2-fold more intense than peaks from the peptide RLSSLRASTSKSESSQK (SEQ ID NO: 7) that contained 4 or 5 phosphates, which in turn were about 3-fold more intense than peaks from the same peptide containing 6 or 7 phosphates. Signal from VADPDHDHTGFL[pT]E[pY]VATR (SEQ ID NO: 29) (Erk2) near m/z of 2305.3 was 5- to 20-fold stronger compared to signal from IADPEHDHTGFL[pT]E[pY]VATR (SEQ ID NO: 30) (Erk1) near m/z of 2333.3.

Accordingly, as shown in Table 3, it is possible to include the relative peak intensity data in the microarray decoding table, which in this case is given for a specific cell line (e.g. MKN-45), specific treatment conditions (e.g. DMSO treatment or a kinase inhibitor treatment), and specific digestion conditions (e.g. mass spec sequencing grade trypsin). Relative intensity of peaks in a mass spectrum is often directly related to relative amounts of the corresponding analytes in a sample and providing such information in the decoding table may assist in the identification of the target analytes. Specifically, data in Table 3 indicates that a proteolytic fragment of Erk2 that is doubly phosphorylated at Thr185 and Tyr187 is more abundant in trypsin-digested MKN-45 cell lysates than a proteolytic fragment of Erk1 that is doubly phosphorylated at Thr202 and Tyr204. In some cases, the relationship between the intensity of a signal in a mass spectrum and the analyte abundance in a sample is more complex, e.g. for peptides with variable numbers of PTM sites. Nevertheless, providing a spectral pattern that includes abundance data in a microarray decoding table is a useful method of identifying the target. For example, while both Phospho-S6 Ribosomal Protein (Ser235/236) and Phospho-p44/42 MAPK (Erk1/2) (Thr202/Tyr204) reactive sites are able to specifically bind a target with a molecular weight near 2333 Da, the microarray decoding table containing abundance information can help provide unambiguous assignment of the detected target analyte. In this Example, two targets recognized by distinct capture agents of the microarray have molecular weights that differ by less than 1 Da (2332.9 and 2333.3), while molecular weights of other targets recognized by the capture agents are separated by at least 5 Da to ensure unambiguous assignment.

TABLE 3

Microarray decoding table including an estimate of relative target abundance

| Reactive Site | Target Sequence | SEQ ID NO: | m/z | Comments |
|---|---|---|---|---|
| 4E-BP1 total | AGGEESQFEMDI | 2 | 1313.4 | 1469 peak is about 10-fold stronger than 1313 peak |
|  | RAGGEESQFEMDI | 1 | 1469.6 |  |
| Phospho-S6 Ribosomal Protein (Ser235/236) | RLSSLRASTSKSESSQK: 2P | 7 | 2013.1 | 2013 and 2093 peaks have similar intensity and are about 2-fold stronger than 2173 and 2252 peaks. 2173 and 2252 peaks are about 3-fold stronger than 2332 and 2412 peaks |
|  | RLSSLRASTSKSESSQK: 3P | 7 | 2093.0 |  |
|  | RLSSLRASTSKSESSQK: 4P | 7 | 2173.0 |  |
|  | RLSSLRASTSKSESSQK: 5P | 7 | 2252.9 |  |
|  | RLSSLRASTSKSESSQK: 6P | 7 | 2332.9 |  |
|  | RLSSLRASTSKSESSQK: 7P | 7 | 2412.9 |  |
| Phospho-p44/42 MAPK (Erk1/2) (Thr202/Tyr204) | VADPDHDHTGFLT*EY*VATR | 29 | 2305.3 | 2305 peak is about 5 to 20-fold stronger than 2333 peak |
|  | IADPEHDHTGFLT*EY*VATR | 30 | 2333.3 |  |

Example 19

Microarray Configured for Measuring PTM Status of Multiple Sites within a Protein The target analyte is human S6 ribosomal protein, also known as ribosomal protein S6 (rpS6, UniProt entry number P62753) that was described in the previous Examples. According to the online database of protein post-translational modifications (PhosphoSitePlus®), rpS6 may be phosphorylated at multiple sites including a cluster of residues located at the protein C-terminus: Ser235, Ser236, Ser240, Ser242, Ser244, Ser246, Ser247.

A microarray for measuring phosphorylation status of individual sites within rpS6 was produced using previously described methods. The microarray included three different antibodies, which were individually conjugated to their respective beads: (1) the previously described monoclonal rabbit antibody, catalog No. 4858 from Cell Signaling Technology; (2) a polyclonal rabbit antibody, catalog No. E-AB-32812 from Elabscience (Houston, Tex.); (3) a polyclonal rabbit antibody, catalog No. E-AB-32813, also from Elabscience. According to the product description available on Elabscience's website, the immunogen for E-AB-32812 is a synthetic peptide derived from human rpS6 "around the non-phosphorylation site of Ser235", while the immunogen for E-AB-32813 is a synthetic peptide derived from human rpS6 "around the non-phosphorylation site of Ser240". The reactive site that contains antibody #4858 is expected to bind proteolytic fragments of rpS6 that are dually phosphorylated at Ser235/Ser236, as well as proteolytic fragments phosphorylated at Ser240, Ser242, Ser244, Ser246 and/or Ser247 in addition to Ser235/Ser236. Therefore, the epitope recognized by the capture reagent of this reactive site contains two PTMs while some of the targets that bind to the reactive site contain one or more additional PTMs, which are located outside of the epitope. The reactive site that contains antibody #E-AB-32812 is expected to bind proteolytic fragments of rpS6 containing non-phosphorylated Ser 235. The reactive site that contains antibody #E-AB-32813 is expected to bind proteolytic fragments of rpS6 containing non-phosphorylated Ser 240. Because rpS6 may be phosphorylated at several distinct sites, each of the microarray reactive sites is expected to bind proteolytic peptides that have different molecular weights.

The reactive sites of the fabricated microarray were each reacted with 200 µg of trypsin-digested lysate of MKN-45 cells, which was prepared as previously described. In this Example, each of the microarray reactive sites was individually incubated with the digested lysate and subsequently prepared for MS analysis. Accordingly, the identity of an antibody conjugated to a particular reactive site was known prior to and during the MS analysis. MALDI TOF mass spectra were acquired from individual reactive sites as previously described. The mass spectra of proteolytic peptides captured by the antibody #4858 displayed several prominent peaks near average m/z of 2013.1, 2093.0, 2173.0, 2252.9, 2332.9 and 2412.9, which were assigned to C-terminal fragments of rpS6 (amino acids 233 through 249) containing 2, 3, 4, 5, 6 and 7 phosphorylated sites, respectively. The mass spectra of proteolytic peptides captured by the antibody E-AB-32813 displayed additional peaks near m/z of 1853.1 and 1933.0, which were assigned to C-terminal fragments of rpS6 (amino acids 233 through 249) containing 0 and 1 phosphorylated site, respectively. The 1853.1 and 1933.0 peaks were not detected in the mass spectra obtained using the antibody #4858, which requires a presence of at least 2 phosphorylated sites. Likewise, the 2252.9, 2332.9 and 2412.9 peaks were not detected in the mass spectra obtained using the antibody E-AB-32813, which requires a presence of at least one and possibly more non-phosphorylated sites. The mass spectra obtained using the antibody E-AB-32812 displayed a weak peak near m/z of 1853.1 corresponding to the non-phosphorylated C-terminal fragment of rpS6 and no detectable peaks at higher m/z. The low intensity of this signal may be due to the more efficient trypsin digestion of non-phosphorylated rpS6, which contains several internal Arg and Lys residues, compared to its phosphorylated counterpart. This Example shows a microarray that contains distinct capture agents that specifically recognize distinct epitopes in a sequence of a naturally occurring protein, with distinct capture agents being associated with distinct beads. It also shows a microarray that contains distinct capture agents that specifically recognize a protein site (Ser235 in rpS6) in the absence and in the presence of a PTM, in this case phosphorylation.

Example 20

Microarray for Measuring Multiple Proteolytic Fragments of a Protein

The protein is the previously described human eukaryotic translation initiation factor 4E-binding protein 1 (4E-BP1, UniProt entry number Q13541). According to the PhosphoSitePlus® database, 4E-BP1 may be phosphorylated at multiple sites including Thr37, Thr46, Ser65, Thr70, Ser101 and Ser112.

A microarray for measuring phosphorylation status of individual sites within 4E-BP1 was produced using the previously described methods. The microarray included 4 antibodies, all purchased from Cell Signaling Technology, which were individually conjugated to their respective beads: (1) phospho-4E-BP1 (Thr37/46) (236B4) rabbit mAb (catalog No. 2855); (2) phospho-4E-BP1 (Ser65) (D9G1Q) rabbit mAb (catalog No. 13443); (3) phospho-4E-BP1 (Thr70) (D7F61) rabbit mAb (catalog No. 13396) and (4) 4E-BP1 (53H11) rabbit mAb (catalog No. 9644). The first 3 antibodies on this list are designed to recognize corresponding phosphorylated sites of human 4E-BP1 while the #9644 antibody is designed to probe the total amount of 4E-BP1. Thus, the microarray contained 4 distinct reactive sites that were able to probe different sites within 4E-BP1. The microarray contained fewer than 5 replicates of each of the 4 distinct reactive sites.

According to the product description on the manufacturer's website, the #9644 antibody "is produced by immunizing rabbits with a synthetic peptide corresponding to residues surrounding Ser112 of human 4E-BP1". It was experimentally verified that the reactive site containing this antibody efficiently captured a synthetic peptide containing sequence RAGGEESQFEMDI (SEQ ID NO: 1) but did not bind a peptide containing sequence RAGGEE[pS]QFEMDI (SEQ ID NO: 31), in which residue corresponding to Ser112 of 4E-BP1 was phosphorylated. Thus, the #9644 antibody specifically recognized a non-phosphorylated peptide in a presence of a phospho peptide containing the same amino acid sequence.

The fabricated microarray was incubated with 200 µg of trypsin-digested lysate of MKN-45 cells, which was prepared as previously described. The peptides captured on individual reactive sites were measured by linear and reflector MALDI TOF MS and also subjected to MS-MS sequencing using the LIFT mode of Bruker Autoflex. After the sequences of peptides captured on individual reactive sites were determined by LIFT, it was possible to assign them to each of the 4 antibodies included in the array, based on the antibody specificity. The reactive site containing #9644 antibody captured peptides RAGGEESQFEMDI (SEQ ID NO: 1) (1 missed cleavage, MW 1469.57) and AGGEESQFEMDI (SEQ ID NO: 2) (0 missed cleavages, MW 1313.39). The reactive site containing #2855 antibody captured peptides VVLGDGVQLPPGDYST[pT]PGGTLFSTTPGGTR (SEQ ID NO: 32) (0 missed cleavages, MW 3129.36), VVLGDGVQLPPGDYSTTPGGTLFST[pT]PGGTR (SEQ ID NO: 33) (0 missed cleavages, MW 3129.36) and VVLGDGVQLPPGDYST[pT]PGGTLFST[pT]PGGTR (SEQ ID NO: 34) (0 missed cleavages, MW 3209.3449). In addition, peptides containing 1 and 2 missed cleavage sites such as VVLGDGVQLPPGDYST[pT]PGGTLFSTTPGGTRIIYDRK (SEQ ID NO: 35) were also captured. The reactive site containing #13443 antibody captured peptides FLME[camC]RN[pS]PVTKTPPR (SEQ ID NO: 36) (2 missed cleavage sites, MW 2014.28) and FLME[camC]RN[pS]PVTKTPPRDLPTIPGVTSPSS-DEPPMEASQSHLR (SEQ ID NO: 37) (3 missed cleavage sites, MW 4745.29). The reactive site containing #13396 antibody captured peptides FLME[camC]RNSPVTK[pT]PPR (SEQ ID NO: 38) (2 missed cleavage sites, MW 2014.28) and FLME[camC]RNSPVTK[pT]PPRDLPTIPGVTSPSSDEPPMEASQSHLR (SEQ ID NO: 39) (3 missed cleavage sites, MW 4745.29). [camC] denotes carbamidomethyl cysteine. All peptides had natural isotope abundance.

In this Example, the microarray contained distinct capture agents, namely antibodies #13443 and #13396, which were associated with distinct beads and which individually recognized distinct epitopes containing phospho-Ser65 and phospho-Thr70, respectively, within a fragment of human 4E-BP1 that has a molecular weight less than 5000 Da. The site of the first PTM (phospho-Ser65) is separated from the site of the second PTM (phospho-Thr70) by less than 10 amino acids.

In this Example, the epitope recognized by the antibody #2855, namely the ST[pT]P sequence (SEQ ID NO: 40) occurs naturally in both human and mouse 4E-BP1.

In this Example, the epitopes recognized by the antibodies #2855 and #9644 lack proteolytic cleavage sites that are recognized by trypsin and chymotrypsin.

In this Example, three distinct PTM-containing fragments of a protein were captured on distinct reactive sites of the microarray.

In this Example, the antibodies used for capturing proteolytic peptides have been validated by the manufacturer for assays including western blot, immunoprecipitation, immunofluorescence, immunohistochemistry, flow cytometry and ELISA.

The sequence length of 4E-BP1 is 118 amino acids. The length of proteolytic fragments of 4E-BP1, which were captured by individual reactive sites of the microarray, ranged from 13 amino acids to 42 amino acids. The combined sequence length of all non-overlapping proteolytic fragments that were captured by the microarray was 86 amino acids, more than 70% of the sequence length of the protein. In this Example, it was possible to probe a substantial portion of a protein, e.g. more than 50% of a sequence length of a protein using a microarray containing fewer than 10 distinct capture agents.

In a separate experiment, the same microarray was reacted with a chymotrypsin-digested lysate of MKN-45 cells. The reactive site containing antibody #9644 captured peptides RNSPEDKRAGGEESQFEMDI (SEQ ID NO: 41) (1 missed cleavage site, MW 2296.44) and RN[pS]PEDKRAGGEESQFEMDI (SEQ ID NO: 42) (1 missed cleavage site, MW 2376.42). The epitope recognized by the capture agent of this reactive site did not contain a PTM, while one of the captured peptide targets contained the PTM, namely, phosphorylation, in a position corresponding to Ser101 of human 4E-BP1.

Example 21

Microarray Reactive Site Configured for Binding a Target Containing Different PTM Types R&D Systems (Minneapolis, Minn.) Human/Mouse/Rat Phospho-CDC2/CDK1 (Y15) antibody, catalog No. AF888 recognizes a chymotrypsin-digested fragment of human cyclin-dependent kinase 2 (UniProt entry number P24941) [Ac]MENFQKVEKIGEGT[pY]GVVY (SEQ ID NO: 43) (2 missed cleavages, MW 2314.52), which contains both acetylation at the N-terminus and phosphorylation of the amino acid corresponding to Tyr15 of human CDC2. The first PTM (phosphorylation) is located within the epitope, while the second PTM (acetylation) is located outside of the epitope. In this Example, the site of the first PTM is separated from the site of the second PTM by more than 10 amino acids within a peptide that has a molecular weight less than 4000 Da.

Example 22

Capture Agent Configured for Binding Targets Derived from Distinct Proteins that are Constituents of Distinct Biological Pathways An antibody that recognizes an amino acid sequence PKEAP (SEQ ID NO: 44), which is found in human STAT1 (UniProt entry number P42224), also recognizes an amino acid sequence PKPAP (SEQ ID NO: 45), which is found in transcription factor p65 (UniProt entry number Q04206). The former protein is signal transducer and transcription activator while the latter is a transcription factor. MALDI MS-detectable fragments of STAT1 and p65 containing these sequences can be produced by chymotrypsin digestion of their respective precursor proteins in lysates of MKN-45 cells using previously described methods. Such antibody is available from Cell Signaling Technology as Stat1 (D1K9Y) Rabbit mAb, catalog number #14994.

Example 23

Microarray Configured for Binding Intact Protein and Small Molecule Target Analytes The microarray included antibodies that have been validated by their respective manufacturers to recognize intact, i.e. non-digested, proteins and small molecule targets. Mouse monoclonal antibody recognizing human insulin (MW 5807.6 Da) was from Novus Biologicals, catalog number NBP2-32975. Rabbit polyclonal antibody recognizing full-length human C Reactive Protein (MW 25039 Da) was from Abcam, product code ab31156. Mouse monoclonal antibody recognizing cortisol (MW 362.46) was from Abcam, product code ab116600. Mouse monoclonal antibody recognizing testosterone (MW 288.43) was from Novus Biologicals, catalog number NBP1-78562.

The microarray contained antibodies that recognize small molecules with MW less than 700 Da, as well as antibodies that recognize intact proteins with MW greater than 5000 Da and 10000 Da (insulin and CRP, respectively).

The microarray also contained beads conjugated to Protein A+G. In the absence of cross-linking, the antibodies listed in this Example were eluted from the Protein A+G conjugated beads and detected by MALDI TOF MS using sinapinic acid as the matrix. The antibodies were detected in the molecular weight range between approximately 130 kDa and 170 kDa, depending on the specific antibody sequence. This Example shows that Protein A+G may serve as the capture reagent for binding proteins, e.g. antibodies that have molecular weight greater than 100 kDa.

All patents, patent applications, and published references cited herein are hereby incorporated by reference in their entirety. While the present disclosure has been described in connection with the specific embodiments thereof, it will be understood that it is capable of further modification. Furthermore, this application is intended to cover any variations, uses, or adaptations of the disclosure, including such departures from the present disclosure as come within known or customary practice in the art to which the disclosure pertains, and as fall within the scope of the appended claims.

What is claimed is:

1. A bead array system adapted for use in analyzing a sample to identify at least one target therein from amongst a set of potential targets that may be present in the sample and whose identities are known, the bead array system comprising:
a bead array, the bead array comprising
a first reactive site, the first reactive site comprising a first bead and multiple copies of a first capture agent associated with the first bead, wherein each copy of the first capture agent specifically recognizes a first epitope and is configured to specifically bind, but has not yet bound to, any one of a plurality of first reactive site potential targets containing the first epitope, the plurality of first reactive site potential targets comprising a first target and a second target, a molecular weight of each of the first reactive site potential targets being different, and
a second reactive site, the second reactive site comprising a second bead and multiple copies of a second capture agent associated with the second bead, the second capture agent being distinct from the first capture agent, wherein each copy of the second capture agent specifically recognizes a second epitope and is configured to specifically bind, but has not yet bound to, any one of at least one second reactive site potential target containing the second epitope, the at least one second reactive site potential target comprising a third target, and a decoding table in an electronic medium, the decoding table being configured to determine the identity of each target that will bind to the first capture agent or the second capture agent, the decoding table containing information that is collected prior to contacting the sample with the first and second reactive sites, said information comprising a first set of values and a second set of values, the first set of values comprising, for each of the plurality of first reactive site potential targets, a value that is derived from its molecular weight, the second set of values comprising, for each of the at least one second reactive site potential target, a value that is derived from its molecular weight, said information further comprising expected abundances of the first and the second target in the sample.

2. The bead array system of claim 1 wherein the first target is a proteolytic fragment of a naturally occurring protein and the second target is a synthetic peptide.

3. The bead array system of claim 1 wherein the first target is a phosphorylated fragment of a first protein and the second target is a phosphorylated fragment of a second protein, the first and the second proteins being constituents of distinct biological pathways.

4. The bead array system of claim 1 wherein the first target is a fragment of a human protein and the second target is a fragment of a mouse protein.

5. The bead array system of claim 1 wherein the first target lacks a post-translational modification (PTM) and the second target contains the PTM.

6. The bead array system of claim 1 wherein the first target contains a first post-translational modification (PTM) and the second target contains a second PTM, the first PTM being phosphorylation, the second PTM being one of acetylation, methylation, glycosylation, ubiquitination and sumoylation.

7. A method for identifying a target within a sample, the method comprising the steps of:
   (a) providing the bead array system of claim 1,
   (b) then, contacting the sample with the first reactive site and the second reactive site of the bead array system, whereby one or more targets in the sample bind to the first reactive site,
   (c) then, for each target bound to the first reactive site, obtaining a value corresponding in type to the first set of values in the decoding table, and
   (d) then, using the decoding table to identify each target of step (c).

8. The method of claim 7 wherein the molecular weight of the first target differs from a molecular weight of the third target by less than 1 Da.

9. The method of claim 7 wherein the value is obtained using mass spectrometry and wherein the mass spectrometry is linear time-of-flight (TOF) mass spectrometry.

10. The method of claim 7 wherein a difference between the molecular weight of the first target and the molecular weight of the second target is greater than 5 Da.

11. The method of claim 7 wherein said value obtaining step comprises detecting two or more signals in a mass spectrum.

* * * * *

```
                        SEQUENCE LISTING

<160> NUMBER OF SEQ ID NOS: 45

<210> SEQ ID NO 1
<211> LENGTH: 13
<212> TYPE: PRT
<213> ORGANISM: Homo sapiens

<400> SEQUENCE: 1

Arg Ala Gly Gly Glu Glu Ser Gln Phe Glu Met Asp Ile
1               5                   10

<210> SEQ ID NO 2
<211> LENGTH: 12
<212> TYPE: PRT
<213> ORGANISM: Homo sapiens

<400> SEQUENCE: 2

Ala Gly Gly Glu Glu Ser Gln Phe Glu Met Asp Ile
1               5                   10

<210> SEQ ID NO 3
<211> LENGTH: 31
<212> TYPE: PRT
<213> ORGANISM: Homo sapiens

<400> SEQUENCE: 3

Val Val Leu Gly Asp Gly Val Gln Leu Pro Pro Gly Asp Tyr Ser Thr
1               5                   10                  15

Thr Pro Gly Gly Thr Leu Phe Ser Thr Thr Pro Gly Gly Thr Arg
            20                  25                  30

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Phospho-Tyr

<400> SEQUENCE: 4

Asp Met Tyr Asp Lys Glu Tyr Tyr Ser Val His Asn Lys
1               5                   10

<210> SEQ ID NO 5
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Phospho-Tyr

<400> SEQUENCE: 5

Asp Met Tyr Asp Lys Glu Tyr Tyr Ser Val His Asn Lys Thr Gly Ala
1               5                   10                  15

Lys

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Phospho-Tyr

<400> SEQUENCE: 6

Asp Met Tyr Asp Lys Glu Tyr Tyr Ser Val His Asn Lys Thr Gly Ala
1               5                   10                  15

Lys Leu Pro Val Lys
            20

<210> SEQ ID NO 7
<211> LENGTH: 17
<212> TYPE: PRT
<213> ORGANISM: Homo sapiens

<400> SEQUENCE: 7

Arg Leu Ser Ser Leu Arg Ala Ser Thr Ser Lys Ser Glu Ser Ser Gln
1               5                   10                  15

Lys

<210> SEQ ID NO 8
<211> LENGTH: 15
<212> TYPE: PRT
<213> ORGANISM: Homo sapiens

<400> SEQUENCE: 8

Gln Asp Thr Tyr Gln His Pro Pro Lys Asp Ser Ser Gly Gln His
1               5                   10                  15

<210> SEQ ID NO 9
<211> LENGTH: 41
<212> TYPE: PRT
<213> ORGANISM: Homo sapiens

<400> SEQUENCE: 9

Leu Glu Ala Pro Asp Ala Asp Glu Leu Pro Lys Gly Glu Phe Asp Pro
1               5                   10                  15

Gly Gln Asp Thr Tyr Gln His Pro Pro Lys Asp Ser Ser Gly Gln His
            20                  25                  30

Val Asp Val Ser Pro Thr Ser Gln Arg
        35                  40

<210> SEQ ID NO 10
<211> LENGTH: 43

```
<212> TYPE: PRT
<213> ORGANISM: Homo sapiens

<400> SEQUENCE: 10

Phe Arg Leu Glu Ala Pro Asp Ala Asp Glu Leu Pro Lys Gly Glu Phe
1               5                   10                  15

Asp Pro Gly Gln Asp Thr Tyr Gln His Pro Pro Lys Asp Ser Ser Gly
            20                  25                  30

Gln His Val Asp Val Ser Pro Thr Ser Gln Arg
        35                  40

<210> SEQ ID NO 11
<211> LENGTH: 34
<212> TYPE: PRT
<213> ORGANISM: Mus musculus

<400> SEQUENCE: 11

Phe Lys Leu Glu Ala Pro Asp Ala Asp Glu Leu Pro Arg Ser Asp Phe
1               5                   10                  15

Asp Pro Gly Gln Asp Thr Tyr Gln His Pro Pro Lys Asp Ser Ser Gly
            20                  25                  30

Gln Arg

<210> SEQ ID NO 12
<211> LENGTH: 35
<212> TYPE: PRT
<213> ORGANISM: Mus musculus

<400> SEQUENCE: 12

Lys Phe Lys Leu Glu Ala Pro Asp Ala Asp Glu Leu Pro Arg Ser Asp
1               5                   10                  15

Phe Asp Pro Gly Gln Asp Thr Tyr Gln His Pro Pro Lys Asp Ser Ser
            20                  25                  30

Gly Gln Arg
        35

<210> SEQ ID NO 13
<211> LENGTH: 12
<212> TYPE: PRT
<213> ORGANISM: Homo sapiens

<400> SEQUENCE: 13

Phe Ser Thr Thr Pro Gly Gly Thr Arg Ile Ile Tyr
1               5                   10

<210> SEQ ID NO 14
<211> LENGTH: 11
<212> TYPE: PRT
<213> ORGANISM: Homo sapiens

<400> SEQUENCE: 14

Ser Thr Thr Pro Gly Gly Thr Arg Ile Ile Tyr
1               5                   10

<210> SEQ ID NO 15
<211> LENGTH: 17
<212> TYPE: PRT
<213> ORGANISM: Homo sapiens

<400> SEQUENCE: 15

Phe Ser Thr Thr Pro Gly Gly Thr Arg Ile Ile Tyr Asp Arg Lys Phe
1               5                   10                  15
```

Leu

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phospho-Thr

<400> SEQUENCE: 16

Ser Thr Thr Pro Gly Gly Thr Leu
1               5

<210> SEQ ID NO 17
<211> LENGTH: 11
<212> TYPE: PRT
<213> ORGANISM: Homo sapiens

<400> SEQUENCE: 17

Gly Gly Glu Glu Ser Gln Phe Glu Met Asp Ile
1               5                   10

<210> SEQ ID NO 18
<211> LENGTH: 18
<212> TYPE: PRT
<213> ORGANISM: Homo sapiens

<400> SEQUENCE: 18

Lys Ala Gln Lys Lys Asp Gly Lys Lys Arg Lys Arg Ser Arg Lys Glu
1               5                   10                  15

Ser Tyr

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Gln His Val Asp Val Ser Pro Thr Ser Gln Arg Leu Gln
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Gln Asp Thr Tyr Gln His Pro Pro Lys Asp Ser Ser Gly Gln His
1               5                   10                  15

<210> SEQ ID NO 21
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 21

Cys Tyr Arg Glu His Arg Ser Glu Leu Asn Leu Arg Arg
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Thr Thr Asp Phe Ile Lys Ser Val Ile Gly His Leu Gln Thr Lys
1               5                   10                  15

<210> SEQ ID NO 23
<211> LENGTH: 21
<212> TYPE: PRT
<213> ORGANISM: Homo sapiens

<400> SEQUENCE: 23

Gln His Pro Pro Lys Asp Ser Ser Gly Gln His Val Asp Val Ser Pro
1               5                   10                  15

Thr Ser Gln Arg Leu
            20

<210> SEQ ID NO 24
<211> LENGTH: 28
<212> TYPE: PRT
<213> ORGANISM: Homo sapiens

<400> SEQUENCE: 24

Gln His Val Asp Val Ser Pro Thr Ser Gln Arg Leu Gln Leu Leu Glu
1               5                   10                  15

Pro Phe Asp Lys Trp Asp Gly Lys Asp Leu Glu Asp
            20                  25

<210> SEQ ID NO 25
<211> LENGTH: 8
<212> TYPE: PRT
<213> ORGANISM: Unknown
<220> FEATURE:
<223> OTHER INFORMATION: Description of Unknown:
      GPI reactive site peptide

<400> SEQUENCE: 25

Tyr Arg Glu His Arg Ser Glu Leu
1               5

<210> SEQ ID NO 26
<211> LENGTH: 19
<212> TYPE: PRT
<213> ORGANISM: Unknown
<220> FEATURE:
<223> OTHER INFORMATION: Description of Unknown:
      IDH3 reactive site peptide

<400> SEQUENCE: 26

Ser Thr Thr Thr Asp Phe Ile Lys Ser Val Ile Gly His Leu Gln Thr
1               5                   10                  15

Lys Gly Ser
```

```
<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Gly Val Asn His Glu Lys Tyr Asp Asn Ser Leu Lys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys His Gln Val Val Ser Ser Asp Phe Asn Ser Asp Thr
1               5                   10

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Phospho-Thr
<220> FEATURE:
<221> NAME/KEY: MOD_RES
<222> LOCATION: (15)..(15)
<223> OTHER INFORMATION: Phospho-Tyr

<400> SEQUENCE: 29

Val Ala Asp Pro Asp His Asp His Thr Gly Phe Leu Thr Glu Tyr Val
1               5                   10                  15

Ala Thr Arg

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Phospho-Thr
<220> FEATURE:
<221> NAME/KEY: MOD_RES
<222> LOCATION: (15)..(15)
<223> OTHER INFORMATION: Phospho-Tyr

<400> SEQUENCE: 30

Ile Ala Asp Pro Glu His Asp His Thr Gly Phe Leu Thr Glu Tyr Val
1               5                   10                  15

Ala Thr Arg

<210> SEQ ID NO 31
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phospho-Ser

<400> SEQUENCE: 31

Arg Ala Gly Gly Glu Glu Ser Gln Phe Glu Met Asp Ile
1               5                   10

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Phospho-Thr

<400> SEQUENCE: 32

Val Val Leu Gly Asp Gly Val Gln Leu Pro Pro Gly Asp Tyr Ser Thr
1               5                   10                  15

Thr Pro Gly Gly Thr Leu Phe Ser Thr Thr Pro Gly Gly Thr Arg
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Phospho-Thr

<400> SEQUENCE: 33

Val Val Leu Gly Asp Gly Val Gln Leu Pro Pro Gly Asp Tyr Ser Thr
1               5                   10                  15

Thr Pro Gly Gly Thr Leu Phe Ser Thr Thr Pro Gly Gly Thr Arg
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Phospho-Thr
<220> FEATURE:
<221> NAME/KEY: MOD_RES
<222> LOCATION: (26)..(26)
<223> OTHER INFORMATION: Phospho-Thr

<400> SEQUENCE: 34

Val Val Leu Gly Asp Gly Val Gln Leu Pro Pro Gly Asp Tyr Ser Thr
1               5                   10                  15
```

Thr Pro Gly Gly Thr Leu Phe Ser Thr Thr Pro Gly Gly Thr Arg
            20                  25                  30

<210> SEQ ID NO 35
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Phospho-Thr

<400> SEQUENCE: 35

Val Val Leu Gly Asp Gly Val Gln Leu Pro Gly Asp Tyr Ser Thr
1               5                   10                  15

Thr Pro Gly Gly Thr Leu Phe Ser Thr Thr Pro Gly Gly Thr Arg Ile
            20                  25                  30

Ile Tyr Asp Arg Lys
        35

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Carbamidomethyl Cys
<220> FEATURE:
<221> NAME/KEY: MOD_RES
<222> LOCATION: (8)..(8)
<223> OTHER INFORMATION: Phospho-Ser

<400> SEQUENCE: 36

Phe Leu Met Glu Cys Arg Asn Ser Pro Val Thr Lys Thr Pro Pro Arg
1               5                   10                  15

<210> SEQ ID NO 37
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Carbamidomethyl Cys
<220> FEATURE:
<221> NAME/KEY: MOD_RES
<222> LOCATION: (8)..(8)
<223> OTHER INFORMATION: Phospho-Ser

<400> SEQUENCE: 37

Phe Leu Met Glu Cys Arg Asn Ser Pro Val Thr Lys Thr Pro Pro Arg
1               5                   10                  15

Asp Leu Pro Thr Ile Pro Gly Val Thr Ser Pro Ser Ser Asp Glu Pro
            20                  25                  30

Pro Met Glu Ala Ser Gln Ser His Leu Arg
        35                  40

```
<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Carbamidomethyl Cys
<220> FEATURE:
<221> NAME/KEY: MOD_RES
<222> LOCATION: (13)..(13)
<223> OTHER INFORMATION: Phospho-Thr

<400> SEQUENCE: 38

Phe Leu Met Glu Cys Arg Asn Ser Pro Val Thr Lys Thr Pro Pro Arg
1               5                   10                  15

<210> SEQ ID NO 39
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Carbamidomethyl Cys
<220> FEATURE:
<221> NAME/KEY: MOD_RES
<222> LOCATION: (13)..(13)
<223> OTHER INFORMATION: Phospho-Thr

<400> SEQUENCE: 39

Phe Leu Met Glu Cys Arg Asn Ser Pro Val Thr Lys Thr Pro Pro Arg
1               5                   10                  15

Asp Leu Pro Thr Ile Pro Gly Val Thr Ser Pro Ser Ser Asp Glu Pro
            20                  25                  30

Pro Met Glu Ala Ser Gln Ser His Leu Arg
        35                  40

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phospho-Thr

<400> SEQUENCE: 40

Ser Thr Thr Pro
1

<210> SEQ ID NO 41
<211> LENGTH: 20
<212> TYPE: PRT
<213> ORGANISM: Homo sapiens

<400> SEQUENCE: 41

Arg Asn Ser Pro Glu Asp Lys Arg Ala Gly Gly Glu Glu Ser Gln Phe
1               5                   10                  15

Glu Met Asp Ile
```

-continued

```
                        20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phospho-Ser

<400> SEQUENCE: 42

Arg Asn Ser Pro Glu Asp Lys Arg Ala Gly Gly Glu Glu Ser Gln Phe
1               5                   10                  15

Glu Met Asp Ile
            20

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (15)..(15)
<223> OTHER INFORMATION: Phospho-Tyr

<400> SEQUENCE: 43

Met Glu Asn Phe Gln Lys Val Glu Lys Ile Gly Glu Gly Thr Tyr Gly
1               5                   10                  15

Val Val Tyr

<210> SEQ ID NO 44
<211> LENGTH: 5
<212> TYPE: PRT
<213> ORGANISM: Homo sapiens

<400> SEQUENCE: 44

Pro Lys Glu Ala Pro
1               5

<210> SEQ ID NO 45
<211> LENGTH: 5
<212> TYPE: PRT
<213> ORGANISM: Homo sapiens

<400> SEQUENCE: 45

Pro Lys Pro Ala Pro
1               5
```